(12) United States Patent
Chang et al.

(10) Patent No.: US 9,329,191 B2
(45) Date of Patent: May 3, 2016

(54) REACTION-BASED FLUORESCENT PROBE FOR SELECTIVE DETECTION OF CARBON MONOXIDE USING METAL-MEDIATED CARBONYLATION

(71) Applicant: THE REGENTS OF THE UNIVERSITY OF CALIFORNIA, Oakland, CA (US)

(72) Inventors: Christopher J. Chang, Berkeley, CA (US); Brian William Michel, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/010,327

(22) Filed: Aug. 26, 2013

(65) Prior Publication Data

US 2015/0057185 A1 Feb. 26, 2015

(51) Int. Cl.
*G01N 33/84* (2006.01)
*C07F 15/00* (2006.01)
*G01N 33/58* (2006.01)

(52) U.S. Cl.
CPC .............. *G01N 33/84* (2013.01); *C07F 15/006* (2013.01); *G01N 33/581* (2013.01)

(58) Field of Classification Search
CPC ..... C07F 15/006; C07F 5/022; G01N 33/581; G01N 33/84
USPC ............. 435/25, 29; 506/11, 12, 15; 548/402, 548/405
See application file for complete search history.

(56) References Cited

U.S. PATENT DOCUMENTS

2008/0274560 A1* 11/2008 Yang et al. .................... 436/124
2011/0245495 A1* 10/2011 Inoue et al. ................... 544/225

OTHER PUBLICATIONS

Michel ("A Reaction-Based Fluorescent Probe for Selective Imaging of Carbon Monoxide in Living Cells Using a Palladium-Mediated Carbonylation" JACS, 2012, 134, 15668-15671).*
Hudson ("Nonconjugated Dimesitylboryl-Functionalized Phenylpyridines and Their Cyclometalated Platinum(II) Complexes" Organometallics, 2011, 30, 4695-4701).*
Lentijo ("Cyclopalladated complexes of perylene imine: Mononuclear complexes with five- or six-membered metallacycles" Dalton Transactions, 2011, 40, 7602-7609).*
Yamada ("A cyclopalladated complex of corannulene with a pyridine pendant and its columnar self-assembly" Dalton Transactions, 2013, 42, 3300-3303).*

(Continued)

*Primary Examiner* — Jafar Parsa
*Assistant Examiner* — Amy C Bonaparte
(74) *Attorney, Agent, or Firm* — Morgan, Lewis & Bockius LLP; Jeffry S. Mann

(57) ABSTRACT

Carbon monoxide (CO) is a member of the gasotransmitter family that includes NO and $H_2S$ and is implicated in a variety of pathological and physiological conditions. Whereas exogenous therapeutic additions of CO to tissues and whole animals have been well studied, the real-time spatial and temporal tracking of CO at the cellular level remains an open challenge. We now report a new type of turn-on fluorescent probe for selective CO detection by exploiting palladium-mediated carbonylation reactivity. The compounds of the invention are capable of detecting CO both in aqueous buffer and in live cells with high selectivity over a range of biologically relevant reactive small molecules, providing a potentially powerful approach for interrogating its chemistry in biological systems.

10 Claims, 23 Drawing Sheets

(56) References Cited

OTHER PUBLICATIONS

La Deda ("Organometallic emitting dyes: Palladium(II) Nile red complexes" Journal of Organometallic Chemistry, 2005, 690, 857-861).*

Slagt ("Pyrenoxy-based NCN-pincer palladium(II) molecular tweezers: Synthesis, properties in solution and catalysis" Eur. J. Org. Chem, 2003,1692-1703).*

Veerman ("Near-Field Scanning Optical Microscopy of Single Fluorescent Dendritic Molecules" J. Phys. Chem. A, 13 (51), 1999, 11264-11270).*

Yuan ("Lighting up Carbon Monoxide: Fluorescent Probes for Monitoring CO in Living Cells" Angew. Chem. Int. Ed., 2013, 52, 1628-1630, first available online on Dec. 13, 2012).*

Kumar ("Recent developments of fluorescent probes for the detection of gasotransmitters (NO, CO and H2S)" Coordination Chemistry Reviews (2013), 257, p. 2335-2347—first available online on Mar. 20, 2013).*

Aguilar, D. et al., Curr. Org. Chem. 2011, 15, 3441-3464.

Barr, N. et al., J. Organomet. Chem. 1986, 302, 117-126.

Chang, M. C. Y. et al.,. J. Am. Chem. Soc. 2004, 126, 15392-15393.

Clark, J. E. et al., Circ. Res. 2003, 93, e2-e8.

Dickinson, B. C.; Chang, C. J., J. Am. Chem. Soc. 2008, 130, 9638-9639.

Dickinson, B. C. et al., Nat. Chem. Biol. 2011, 7, 106-112.

Dupont, J. et al., J. Chem. Rev. 2005, 105, 2527-2571.

Dupont, J. et al., Organometallics 1987, 6, 899-901.

Fuchita, Y. et al., Inorg. Chim. Acta 1995, 233, 91-96.

Li, H. et al., Dalton Trans. 2010, 39, 10442-10446.

Lippert, A. R. et al., J. Am. Chem. Soc. 2011, 133, 10078-10080.

Lippert, A. R. et al., J. Acc. Chem. Res. 2011, 44, 793-804.

Marks, G. S. et al., Antioxid. Redox Signaling 2002, 4, 271-277.

Miller, E. W. et al., J. Am. Chem. Soc. 2005, 127, 16652-16659.

Miller, E. W. et al., Nat. Chem. Biol. 2007, 3, 263-267.

Miller, E. W. et al., Proc. Natl. Acad. Sci. U.S.A. 2010, 107, 15681-15686.

Moragues, M. E., J. Am. Chem. Soc. 2011, 133, 15762-15772.

Morimoto, Y. et al., Am. J. Physiol. 2001, 280.

Ryabov, A. D. Synthesis 1985, 233-252.

Santra, M. et al., Chem. Commun. 2010, 46, 3964-3966.

Srikun, D. et al., J. Am. Chem. Soc. 2008, 130, 4596-4597.

Srikun, D. et al., J. Am. Chem. Soc. 2010, 132, 4455-4465.

Yusop, R. M. et al., Nat. Chem. 2011, 3, 239-243.

* cited by examiner

R = alkyl, fluoroalkyl, alcohols, ethers, thiols, etc.

REACTION-BASED FLUORESCENT PROBE FOR SELECTIVE DETECTION OF CARBON MONOXIDE USING METAL-MEDIATED CARBONYLATION

STATEMENT AS TO RIGHTS TO INVENTIONS MADE UNDER FEDERALLY SPONSORED RESEARCH OR DEVELOPMENT

N/A.

BACKGROUND OF THE INVENTION

Carbon monoxide (CO) is a well know toxic gas, but emerging research also suggest potentially beneficial effects of temporarily increased levels of CO in attenuating deleterious effects of reactive oxygen species (ROS). To date the study and evaluation of the effects of CO have relied on detecting gross anatomical change of some observable parameter, such as infarct size in the studies of CO on ischemia/reperfusion or offline extracellular measurements using myoglobin as a colorimetric readout. These macroscopic and colorimetric outputs do not provide detailed information about cellular signaling pathways. Therefore we sought to develop a small molecule probe for the detection of CO. Similar to other gasotransmitters (NO and $H_2S$) as well as other reactive small molecules such as $H_2O_2$, the use of small molecule turn-on fluorescent probes to investigate the pathways associated with these species has led to a greater understanding of these molecules.

Carbon monoxide (CO) is best known as a toxic gas inhaled from common sources such as smoke and car exhaust, but emerging studies show that this reactive small molecule is also continuously produced in the body from the breakdown of heme via the heme oxygenase enzymes (Tenhunen, R.; Marver, H. S.; Schmid, R. Proc. Nat. Acad. Sci. U.S.A. 1968, 61, 748-755; Maines, M. D. *FASEB J.* 1988, 2, 2557-2568; and Ryter, S. W.; Alam, J.; Choi, A. M. K. *Physiol. Rev.* 2006, 86, 583-650. Similar to the other major gasotransmitter molecules NO and $H_2S$, CO is proposed to play significant roles in modulating responses to both chemical and physical stresses (Motterlini, R.; Otterbein, L. E. *Nat. Rev. Drug Discovery* 2010, 9, 728-743; Mann, B. E. *Top. Organometallic Chem.* 2010, 32, 247-285; Bilban, M.; Haschemi, A.; Wegiel, B.; Chin, B. Y.; Wagner, O.; Otterbein, L. E. *J. Mol. Med.* 2008, 86, 267-279; and Wu, L.; Wang, R. *Pharm. Rev.* 2005, 57, 585-630. In one example, exogenous and endogenous CO can provide protection against tissue damage during myocardial ischemia/reperfusion (Fujimoto, H.; Ohno, M.; Ayabe, S.; Kobayashi, H.; Ishizaka, N.; Kimura, H.; Yoshida, K.-i.; Nagai, R. *Arterioscler. Thromb. Vasc. Biol.* 2004, 24, 1848-1853), and to this end, CO releasing molecules (CORMs) based on transition-metal carbonyl complexes have been developed as potential therapeutics that allow for more targeted release of CO as compared to direct gas inhalation (Motterlini, R.; Otterbein, L. E. *Nat. Rev. Drug Discovery* 2010, 9, 728-743; Motterlini, R.; Clark, J. E.; Foresti, R.; Sarathchandra, P.; Mann, B. E.; Green, C. J. *Circ. Res.* 2002, 90, e17-e24; and Alberto, R.; Motterlini, R. *Dalton Trans.* 2007, 1651-1660).

Despite the important signal/stress dichotomy of CO, many aspects of its chemistry in biological systems remain elusive in part due to the lack of ways to selectively tracking this transient small molecule within intact, living biological specimens. Indeed, the primary methods for interrogating the biological effects of CO to date involve detecting a gross anatomical change of some observable parameter, such as infarct size in studying the effects of CO on ischemia/reperfusion, or offline extracellular measurements using myoglobin (Morimoto, Y.; Durante, W.; Lancaster, D. G.; Klattenhoff, J.; Tittel, F. K. *Am. J. Physiol.* 2001, 280, H483-H488; and Marks, G. S.; Vreman, H. J.; McLaughlin, B. E.; Brien, J. F.; Nakatsu, K. *Antioxid. Redox Signaling* 2002, 4, 271-277) or dirhodium-supported particles (Moragues, M. E.; Esteban, J.; Ros-L is, J. V.; Martinez-Manez, R.; Marcos, M. D.; Martinez, M.; Soto, J.; Sancenon, F. *J. Am. Chem. Soc.* 2011, 133, 15762-15772) for colorimetric readouts. We reasoned that the development of a CO-responsive small-molecule fluorescent probe would meet a critical need for new technologies to monitor this reactive small molecule in biological systems with spatial and temporal information. This approach has proved useful for studying the contributions of a variety of small signal/stress molecules in biological settings (Yang, Y.; Zhao, Q.; Feng, W.; Li, F. *Chem. Rev.* DOI: 10.1021/cr2004103; Kim, H. N.; Lee, M. H.; Kim, H. J.; Kim, J. S.; Yoon, J. *Chem. Soc. Rev.* 2008, 37, 1465-1472; Cho, D.-G.; Sessler, J. L. *Chem. Soc. Rev.* 2009, 38, 1647-1662; Jun, M. E.; Roy, B.; Ahn, K. H. *Chem. Comm.* 2011, 47, 7583-7601; and Du, J.; Hu, M.; Fan, J.; Peng, X. *Chem. Soc. Rev.* 2012, 41, 4511-4535), including NO (Kojima, H.; Nakatsubo, N.; Kikuchi, K.; Kawahara, S.; Kirino, Y.; Nagoshi, H.; Hirata, Y.; Nagano, T. *Anal. Chem.* 1998, 70, 2446-2453; Lim, M. H.; Xu, D.; Lippard, S. J. *Nat. Chem. Biol.* 2006, 2, 375-380; Yang, Y.; Seidlits, S. K.; Adams, M. M.; Lynch, V. M.; Schmidt, C. E.; Anslyn, E. V.; Shear, J. B. *J. Am. Chem. Soc.* 2010, 132, 13114-13116; and Kojima, H.; Hirotani, M.; Nakatsubo, N.; Kikuchi, K.; Urano, Y.; Higuchi, T.; Hirata, Y.; Nagano, T. *Anal. Chem.* 2001, 73, 1967-1973), $H_2S$ (Lippert, A. R.; New, E. J.; Chang, C. J. *J. Am. Chem. Soc.* 2011, 133, 10078-10080; Sasakura, K.; Hanaoka, K.; Shibuya, N.; Mikami, Y.; Kimura, Y.; Komatsu, T.; Ueno, T.; Terai, T.; Kimura, H.; Nagano, T. *J. Am. Chem. Soc.* 2011, 133, 18003-18005; Liu, C.; Pan, J.; Li, S.; Zhao, Y.; Wu, L. Y.; Berkman, C. E.; Whorton, A. R.; Xian, M. *Angew. Chem. Int. Ed.* 2011, 50, 10327-10329; Peng, H.; Cheng, Y.; Dai, C.; King, A. L.; Predmore, B. L.; Lefer, D. J.; Wang, B. *Angew. Chem. Int. Ed.* 2011, 50, 9672-9675; Qian, Y.; Karpus, J.; Kabil, O.; Zhang, S.-Y.; Zhu, H.-L.; Banerjee, R.; Zhao, J.; He, C. *Nat. Commun.* 2011, 2, 495; Yu, F.; Li, P.; Song, P.; Wang, B.; Zhao, J.; Han, K. *Chem. Commun.* 2012, 48, 2852-2854; and Montoya, L. A.; Pluth, M. D. *Chem. Commun.* 2012, 48, 4767-4769), and $H_2O_2$ (Lippert, A. R.; Van, d. B. G. C.; Chang, C. J. *Acc. Chem. Res.* 2011, 44, 793-804; Chang, M. C. Y.; Pralle, A.; Isacoff, E. Y.; Chang, C. J. *J. Am. Chem. Soc.* 2004, 126, 15392-15393; Miller, E. W.; Albers, A. E.; Pralle, A.; Isacoff, E. Y.; Chang, C. J. *J. Am. Chem. Soc.* 2005, 127, 16652-16659; Miller, E. W.; Tulyanthan, O.; Isacoff, E. Y.; Chang, C. J. *Nat. Chem. Biol.* 2007, 3, 263-267; Srikun, D.; Miller, E. W.; Domaille, D. W.; Chang, C. J. *J. Am. Chem. Soc.* 2008, 130, 4596-4597; Dickinson, B. C.; Chang, C. J. *J. Am. Chem. Soc.* 2008, 130, 9638-9639; Miller, E. W.; Dickinson, B. C.; Chang, C. J. *Proc. Natl. Acad. Sci. U.S.A.* 2010, 107, 15681-15686; Srikun, D.; Albers, A. E.; Nam, C. I.; Iavarone, A. T.; Chang, C. J. *J. Am. Chem. Soc.* 2010, 132, 4455-4465; Dickinson, B. C.; Peltier, J.; Stone, D.; Schaffer, D. V.; Chang, C. J. *Nat. Chem. Biol.* 2011, 7, 106-112; Abo, M.; Urano, Y.; Hanaoka, K.; Terai, T.; Komatsu, T.; Nagano, T. *J. Am. Chem. Soc.* 2011, 133, 10629-10637; and Song, D.; Lim, J. M.; Cho, S.; Park, S.-J.; Cho, J.; Kang, D.; Rhee, S. G.; You, Y.; Nam, W. *Chem. Commun.* 2012, 48, 5449-5451), but there are no reports of analogous indicators for CO. Herein, we present the design, synthesis, and biological evaluation of a new type of chemical reagent for selective CO detection in living cells by exploiting palladium-mediated carbonylation chemistry.

Carbon Monoxide Probe 1 (COP-1) represents a unique first-generation chemical tool that features a robust turn-on response to CO with selectivity over reactive nitrogen, oxygen, and sulfur species and can be used to detect this gasotransmitter in aqueous buffer and in live-cell specimens.

BRIEF SUMMARY OF THE INVENTION

The present invention provides compounds and methods for visualizing CO and determining levels of CO in various non-living and living systems, e.g. live cells. Since CO does not inherently react in a nucleophilic, electrophilic, oxidative, or reductive manner with simple organic molecules, in various embodiments, the present invention takes advantage of the well-known metal coordination and metal mediated reactivity.

CO undergoes coordination with many transition metal complexes. In various embodiments, the compounds of the invention make use of the well known palladium (Pd) mediated carbonylation chemistry as a way to functionalize a fluorescent scaffold with carbon monoxide. The effective incorporation of CO into the profluorescent probe of the invention and the concomitant and reduction of a metal bound to the scaffold (e.g., reduction of Pd from the two plus oxidation state to the zero oxidation) state leads to an increase in fluorescence and effective detection of CO. Exemplary metals of use in the invention include, without limitation, Pd, Ru, Rh, Os, Ir, and Pt.

In various embodiments, the invention provides a cyclopalladated species attached to a fluorescent scaffold. In an exemplary embodiment, the fluorescent moiety of the scaffold is a boron-dipyrromethane (BODIPY) moiety.

In an exemplary embodiment, the compound of the invention is selective or specific for CO in the presence of other gases. In various embodiments, the compound of the invention is selective for CO in the presence of a member selected from a variety of reactive oxygen, sulfur, and nitrogen species.

The invention also provides methods of detecting CO using the compounds of the invention. In an exemplary embodiment, the compound of the invention is used to detect and/or quantitate CO released from a CO releasing molecule (e.g., CORM-3).

Other objects, advantages and embodiments of the invention are apparent from the detailed description that follows.

BRIEF DESCRIPTION OF THE DRAWINGS

FIG. 2A shows an overtime increase in fluorescence emission upon treating COP-1 with CORM-3 and a turn-on fluorescence response of 1 µM COP-1 to 50 µM CORM-3 in pH 7.4 DPBS at 37° C. Excitation was at $\lambda_{ex}$=475 nm and emission was collected between 490 and 630 nm. Time points represented by spectra taken 0, 5, 15, 30, 45, and 60 (red) min after the addition of CORM-3.
FIG. 2B shows fluorescence responses of 1 µM COP-1 to CO and biologically relevant reactive oxygen, nitrogen, and sulfur species. Bars represent normalized integrated fluorescence intensity responses between 490 and 630 nm with excitation at $\lambda_{ex}$=475 nm for 50 µM of respective analytes at t=0, 5, 15, 30, 45 and 60 (red) min. Data were acquired in pH 7.4 DPBS buffer at 37° C. Legend: (1) Control; (2) CORM-3; (3) $H_2O_2$; (4) TBHP; (5) NaOCl; (6) $O2^{·-}$; (7) NO; (8) $ONOO^-$; (9) $H_2S$.
FIG. 3A shows HEK293T cells incubated with COP-1 for 30 min at 37° C.;
FIG. 3B shows HEK293T cells incubated with 5 µM CORM-3 for 45 min at 37° C. and 1 µM COP-1 for the final 30 min;
FIG. 3C shows HEK293T cells incubated with 50 µM CORM-3 for 45 min at 37° C. and 1 µM COP-1 for the final 30 min;
FIG. 3D shows Brightfield image for the cells in (c) overlaid with images of 1 µM Hoescht 33342 stain, scale bar represents 100 µM;
FIG. 3E shows the mean fluorescence intensity of representative images with (1) 1 µM COP-1; (2) 1 µM COP-1 and 5 µM CORM-3; (3) 1 µM COP-1 and 50 µM CORM-3.
FIG. 6A shows HEK293T cells incubates with COP-1 or vehicle control. Legend: (1) Vehicle control; (2) 500 nM COP-1; (3) 1 µM COP-1; (4) 2 µM COP-1; (5) 5 µM COP-1; 10 µM COP-1.
FIG. 6B shows HEK293T cells incubated with COP-1 and 50 µM CORM-3 or vehicle control. Legend: (1) Vehicle Control and 50 µM CORM-3; (2) 500 nM COP-1 and 50 µM CORM-3; (3) 1 µM COP-1 and 50 µM CORM-3; (4) 2 µM COP-1 and 50 µM CORM-3; (5) 5 µM COP-1 and 50 µM CORM-3; 10 µM COP-1 and 50 µM CORM-3.

DETAILED DESCRIPTION OF THE INVENTION

I. Introduction

Figure 1A:
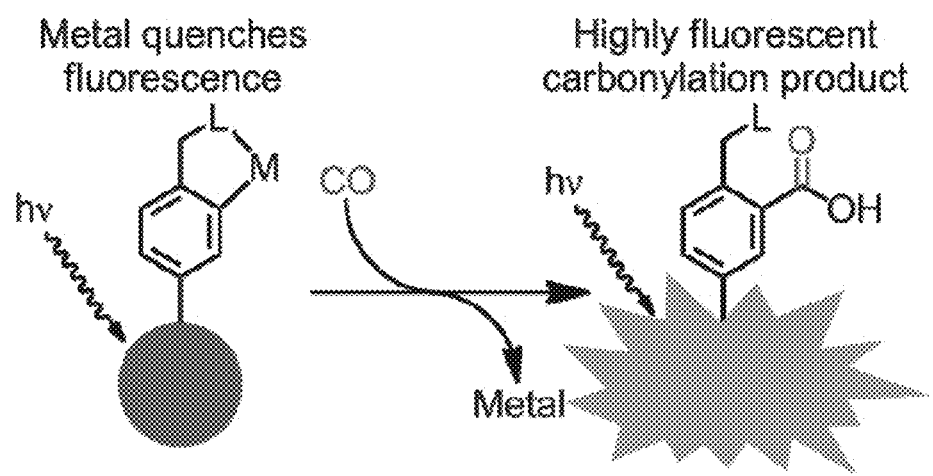
FIG. 1A is a conceptualization of CO detection.
Figure 1B:
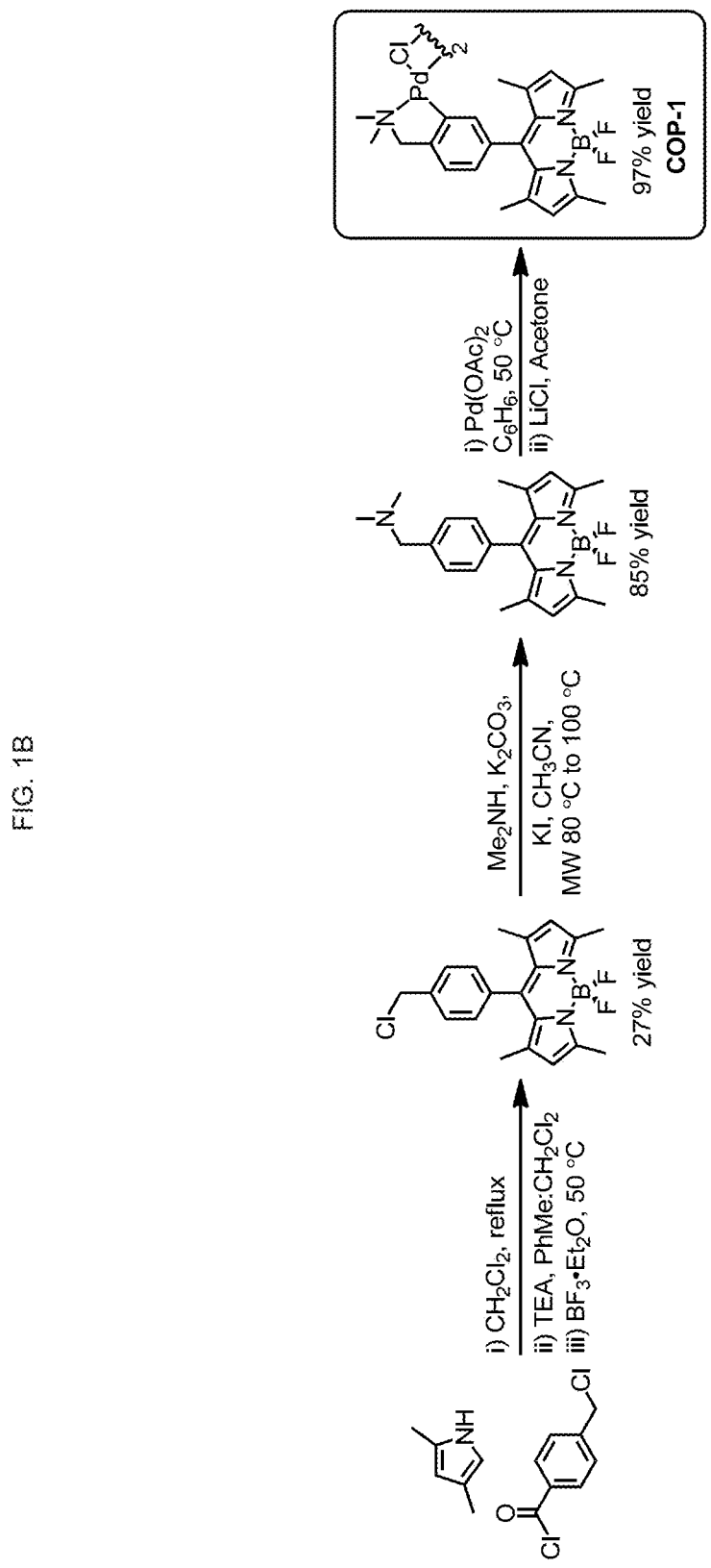
FIG. 1B shows a synthesis of COP-1.
Figure 1C:
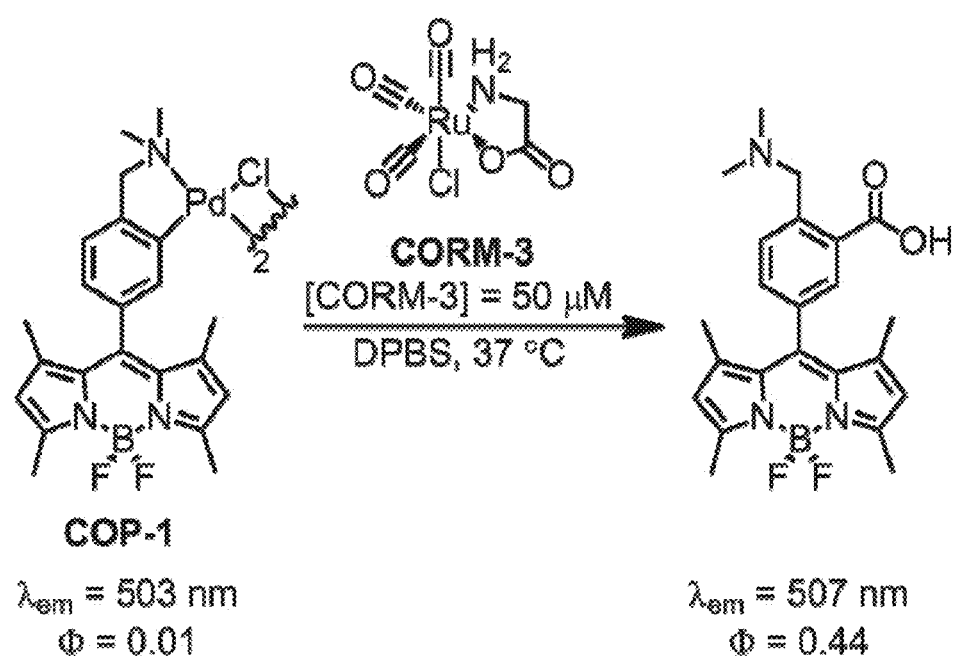
FIG. 1C shows a reaction of COP-1 with CORM-3 and structure of CORM-3.

The present invention provides a class of profluorescent probes that undergo reaction with CO and convert to their fluorescent analogues. The compounds of the invention are of us to detect carbon monoxide (CO). In exemplary embodiments, the profluorescent compounds include a fluorophore and a quencher for that fluorophore within a single molecular scaffold. The probes of the invention can be used as small molecules in solution assays or they can be utilized as a label that is conjugated to a carrier species, such as an analyte or a molecule that interacts with, and allows detection and/or quantification of an analyte. Also provided are methods of using these probes to detect the presence or absence of CO and to quantify the amount of CO in a sample.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In describing the present invention, the following terms will be employed, and are defined as indicated below.

II. Definitions

Where substituent groups are specified by their conventional chemical formulae, written from left to right, the structures optionally also encompass the chemically identical substituents, which would result from writing the structure from right to left, e.g., —$CH_2O$— is intended to also optionally recite —$OCH_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl". Exemplary alkyl groups include the monounsaturated $C_{9-10}$, oleoyl chain or the diunsaturated $C_{9-10, 12-13}$ linoeyl chain.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "aryloxy" and "heteroaryloxy" are used in their conventional sense, and refer to those aryl or heteroaryl groups attached to the remainder of the molecule via an oxygen atom.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2R'$— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Further exemplary cycloalkyl groups include steroids, e.g., cholesterol and its derivatives. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl substituent groups (or rings) that contain from one to four heteroatoms selected from N, O, S, Si and B, wherein the nitrogen and sulfur atoms are optionally oxidized, and the nitrogen atom(s) are optionally quaternized. An exemplary heteroaryl group is a six-membered azine, e.g., pyridinyl, diazinyl and triazinyl. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes aryl, heteroaryl and heteroarene rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl," and "heteroaryl") are meant to optionally include both substituted and unsubstituted forms of the indicated species. Exemplary substituents for these species are provided below.

Substituents for the alkyl and heteroalkyl radicals (including those groups often referred to as alkylene, alkenyl, heteroalkylene, heteroalkenyl, alkynyl, cycloalkyl, heterocyloalkyl, cycloalkenyl, and heterocycloalkenyl) are generically referred to as "alkyl group substituents," and they can be one or more of a variety of groups selected from, but not limited to: H, substituted or unsubstituted aryl, substituted or unsubstituted heteroaryl, substituted or unsubstituted heterocycloalkyl, —OR', =O, =NR', =N—OR', —NR'R", —SR', halogen, —SiR'R"R''', —OC(O)R', —C(O)R', —$CO_2R'$, —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —$NRSO_2R'$, —CN and —$NO_2$ in a number ranging from zero to (2 m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like). These terms encompass groups considered exemplary "alkyl group substituents", which are components of exemplary "substituted alkyl" and "substituted heteroalkyl" moieties.

Similar to the substituents described for the alkyl radical, substituents for the aryl heteroaryl and heteroarene groups are generically referred to as "aryl group substituents." The substituents are selected from, for example: groups attached to the heteroaryl or heteroarene nucleus through carbon or a heteroatom (e.g., P, N, O, S, Si, or B) including, without limitation, substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O) NR'R", —NR"C(O)R', —NR'—C(O)NR"R'", —NR"C(O)$_2$ R', —NR—C(NR'R"R'")=NR"", —NR—C(NR'R") =NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$) alkoxy, and fluoro(C$_1$-C$_4$)alkyl, in a number ranging from zero to the total number of open valences on the aromatic ring system. Each of the above-named groups is attached to the heteroarene or heteroaryl nucleus directly or through a or a heteroatom (e.g., P, N, O, S, Si, or B); and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R""groups when more than one of these groups is present.

Two of the substituents on adjacent atoms of the aryl, heteroarene or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl, heteroarene or heteroaryl ring may optionally be replaced with a substituent of the formula —(CRR')$_s$—X— (CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl. These terms encompass groups considered exemplary "aryl group substituents", which are components of exemplary "substituted aryl" "substituted heteroarene" and "substituted heteroaryl" moieties.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non-aromatic rings. Examples of "fused ring systems" are naphthalenes, indoles, quinolines, chromenes and the like.

As used herein, the term "heteroatom" includes oxygen (O), nitrogen (N), sulfur (S) and silicon (Si) and boron (B).

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl groups.

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), V$_O$GEL'S ENCYCLOPEDIA OF PRACTICAL ORGANIC CHEMISTRY 5$^{TH}$ ED., Longman Scientific and Technical Ltd., Essex, 1991, pp. 809-816; and Heller, *Acc. Chem. Res.* 23: 128 (1990).

As used herein, "energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena.

"Energy transfer pair" is used to refer to a group of molecules that form a single complex within which energy transfer occurs. There is no limitation on the identity of the individual members of the energy transfer pair in this application. All that is required is that the spectroscopic properties of the energy transfer pair as a whole change in some measurable way if the distance between the individual members is altered by some critical amount. An exemplary energy transfer pair of the instant invention is an energy transfer pair internal to a molecule of the invention comprising a fluorophore and a quencher of the fluorophore. In an exemplary embodiment, the compound of the invention includes an internal energy transfer pair formed by a metal atom and a fluorophore. In an exemplary embodiment, the energy transfer pair is disrupted by carbonylation with CO of the moeity to which the metal atom and fluorophore are bound.

As used herein, "fluorescence-modifying group" refers to an atom or other moiety internal to a compound of the invention that can alter in any way the fluorescence emission from the fluorophore internal to a compound of the invention. A fluorescence-modifying group generally accomplishes this through an energy transfer mechanism. Depending on the identity of the fluorescence-modifying group, the fluorescence emission can undergo a number of alterations, including, but not limited to, attenuation, complete quenching, enhancement, a shift in wavelength, a shift in polarity, and a change in fluorescence lifetime. One example of a fluorescence-modifying group is a quenching group.

"Foerster resonance energy transfer" or "FRET" is used interchangeably with FET, and refers to an energy transfer phenomenon in which the light emitted by the excited fluorescent group is absorbed at least partially by a fluorescence-modifying group internal to a compound of the invention (e.g., a metal, M).

The term "ligand" has the meaning ordinarily ascribed to it in the art. Exemplary ligands include at least one donor atom capable of binding to M(0), M(I) or M(II). In an exemplary embodiment, M is a metal that catalyzes carbonylation of an unsaturated system by CO. Exemplary metals, M, include Ru, Rh, Os, Ir, Pt and Pd, e.g., in the zero oxidation state. Ligands can include sterically bulky species, such as substituted or unsubstituted aryl, substituted or unsubstituted heteroaryl and substituted or unsubstituted fused ring systems, secondary and tertiary alkyl groups and the like. Exemplary ligands include, without limitation, H, halogen (i.e., F, Cl, Br, I), substituted or unsubstituted alkyl, nitrogen-containing ligands and oxygen-containing ligands (e.g., nitriles, amines, aminoalcohols, amino acids, phenols), and phosphorus-containing ligands (e.g., phosphines and phosphites).

"CORM" refers to carbon monoxide releasing molecule. See, e.g., *FASEB J.* 2005 February; 19(2):284-6.

The term "salt(s)" includes salts of the compounds prepared by the neutralization of acids or bases, depending on the particular ligands or substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Certain specific compounds of the present invention contain both basic and acidic functionalities that allow the compounds to be converted into either base or acid addition salts. Hydrates of the salts are also included.

As used herein, "linking member" refers to a covalent chemical bond that includes at least one heteroatom. Exemplary linking members include —C(O)NH—, —C(O)O—, —NH—, —S—, —O—, and the like.

The term "targeting group" is intended to mean a moiety that is (1) able to direct a compound of the invention to a target cell, for example to a specific type of tumor cell or (2) is preferentially activated at a target tissue, for example a tumor. The targeting group can be a small molecule. The targeting group can be a nucleic acid, peptide, saccharide, lectin, receptor, ligand for a receptor, and proteins including structural and functional proteins (e.g., albumin, antibodies).

"CORM", as used herein, refers to a CO releasing molecule.

The symbol $\sim\!\sim$, whether utilized as a bond or displayed perpendicular to a bond indicates the point at which the displayed moiety is attached to the remainder of the molecule, solid support, etc.

Below are examples of specific embodiments for carrying out the present invention. The examples are offered for illustrative purposes only, and are not intended to limit the scope of the present invention in any way.

III. Compositions

The compounds and methods of the present invention include numerous advantages over previous assays and methods for studying the role(s) of CO in various systems. For example, the compounds and methods of the invention allow for the direct observation of a fluorescent product that is derived from a direct reaction of a compound of the invention with CO. The compounds of the invention are selective for CO over reactive oxygen, nitrogen and sulfur species, making them valuable for selective biological studies of CO. Reaction based probes, such as those of the invention, are advantageous in that signal builds over time, so small increases in CO levels are detected as compared to a reversible CO binding event.

In an exemplary embodiment, the invention provides a fluorogenic compound, which is a probe for CO, and which detectably fluoresces upon carbonylation with CO, the probe having a structure according to Formula I:

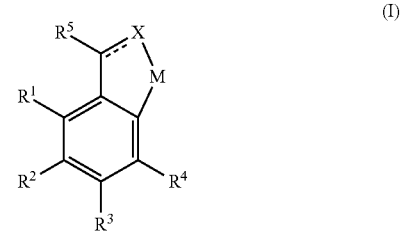

(I)

wherein, M is a metal capable of catalyzing carbonylation by CO of the ring system to which it is bound, the metal optionally bound to one, two or more additional ligands. The dashed line (- - - -) indicates a degree of unsaturation that is either present or absent. X is a moiety selected from $NR^6R^7$, $NR^6$, $PR^6R^7$ and $SR^6$, wherein $R^6$ and $R^7$ are members independently selected from H, substituted or unsubstituted alkyl, substituted or unsubstituted heteroalkyl, substituted or unsubstituted aryl, and substituted or unsubstituted heteroaryl, and $R^6$ and $R^7$, together with the atoms to which they are bound are optionally joined to form a 5- to 7-membered ring system which is a member selected from substituted or unsubstituted cycloalkyl, substituted or unsubstituted heterocycloalkyl, substituted or unsubstituted aryl and substituted or unsubstituted heteroaryl. $R^1$, $R^2$, $R^3$, $R^4$, and $R^5$ are members independently selected from H, substituted or unsubstituted alkyl, substituted or unsubstituted heteroalkyl, substituted or unsubstituted aryl, substituted or unsubstituted heteroaryl, halogen, CN, CF$_3$, acyl, —SO$_2$NR$^{12}$R$^{13}$, —NR$^{12}$R$^{13}$, —OR$^{12}$, —S(O)$_2$R$^{12}$, —C(O)R$^{12}$, —COOR$^{12}$, —CONR$^{12}$R$^{13}$, —S(O)$_2$OR$^{12}$, —OC(O)R$^{12}$, —C(O)NR$^{12}$R$^{13}$, —NR$^{12}$C(O)R$^{13}$, —NR$^{12}$SO$_2$R$^{13}$, —NR$^{12}$C(O)NR$^{13}$R$^{14}$, C(NR$^{12}$)R$^{13}$, and —NO$_2$, and at least one of R$^1$, R$^2$, R$^3$, and R$^4$ is the fluorophore, wherein the fluorophore is maintained in a quenched state by interacting with M. R$^{12}$, R$^{13}$ and R$^{14}$ are members independently selected from H, substituted or unsubstituted alkyl, substituted or unsubstituted heteroalkyl, substituted or unsubstituted aryl, and substituted or unsubstituted heteroaryl, and two or more of R$^{12}$, R$^{13}$, and R$^{14}$, together with the atoms to which they are bound, are optionally joined to form a 5- to 7-membered ring system which is a member selected from substituted or unsubstituted cycloalkyl, substituted or unsubstituted heterocycloalkyl, substituted or unsubstituted aryl and substituted or unsubstituted heteroaryl. Two or more of R$^1$, R$^2$, R$^3$, R$^4$, R$^5$, R$^{12}$, R$^{11}$, R$^{12}$ and R$^{14}$ are optionally joined to form a 5-7-membered ring system selected from substituted or unsubstituted cycloalkyl, substituted or unsubstituted heterocycloalkyl, substituted or unsubstituted aryl and substituted or unsubstituted heteroaryl with the proviso that if two or more of R$^1$, R$^2$, R$^3$, R$^4$, R$^5$, R$^{10}$ and R$^{11}$ are joined to form the ring system, and none of the two or more of R$^1$, R$^2$, R$^3$, R$^4$, R$^5$, R$^6$ and R$^7$ so joined are the fluorophore.

In R$^5$ and R$^{10}$ are joined to form the ring system, e.g., a heteroaryl ring system.

In various embodiments, the invention provides a compound having a structure according to Formula II:

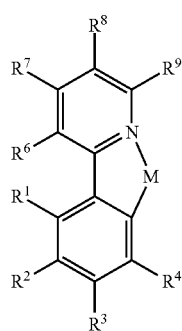

(II)

wherein, R$^6$, R$^7$, R$^8$, and R$^9$ are members independently selected from H, substituted or unsubstituted alkyl, substituted or unsubstituted heteroalkyl, substituted or unsubstituted aryl, substituted or unsubstituted heteroaryl, halogen, CN, CF$_3$, acyl, —SO$_2$NR$^{15}$R$^{16}$, —NR$^{15}$R$^{16}$, —OR$^{15}$, —S(O)$_2$R$^{15}$, —C(O)R$^{15}$, —COOR$^{15}$, —CONR$^{15}$R$^{16}$, —S(O)$_2$OR$^{15}$, —OC(O)R$^{15}$, —C(O)NR$^{15}$R$^{16}$, —NR$^{15}$C(O)R$^{16}$, —NR$^{15}$SO$_2$R$^{16}$, NR$^{15}$, C(O)NR$^{16}$, R$^{17}$, C(NR$^{15}$)R$^{16}$, and —NO$_2$, wherein two or more of R$^{15}$, R$^{16}$, and R$^{17}$, together with the atoms to which they are bound, are joined to form a 5- to 7-membered ring system which is a member selected from substituted or unsubstituted cycloalkyl, substituted or unsubstituted heterocycloalkyl, substituted or unsubstituted aryl and substituted or unsubstituted heteroaryl.

In an exemplary embodiment, the invention provides a compound according to Formula III:

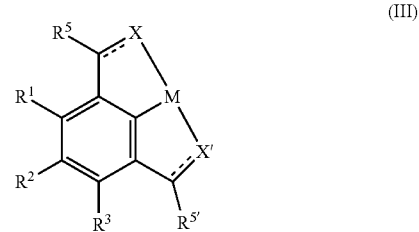

(III)

wherein, X' is a member selected from X is a moiety selected from NR$^{6'}$R$^{7'}$, NR$^{6'}$, PR$^{6'}$R$^{7'}$ and SR$^{6'}$. R$^{6'}$ and R$^{7'}$ are members independently selected from H, substituted or unsubstituted alkyl, substituted or unsubstituted heteroalkyl, substituted or unsubstituted aryl, and substituted or unsubstituted heteroaryl, and R$^{6'}$ and R$^{7'}$, together with the atoms to which they are bound are optionally joined to form a 5- to 7-membered ring system which is a member selected from substituted or unsubstituted cycloalkyl, substituted or unsubstituted heterocycloalkyl, substituted or unsubstituted aryl and substituted or unsubstituted heteroaryl; and R$^{5'}$ is a member selected from H, substituted or unsubstituted alkyl, substituted or unsubstituted heteroalkyl, substituted or unsubstituted aryl, substituted or unsubstituted heteroaryl, halogen, CN, CF$_3$, acyl, —SO$_2$NR$^{12'}$R$^{13'}$, —NR$^{12'}$R$^{13'}$, —OR$^{12'}$, —S(O)$_2$R$^{12'}$, —C(O)R$^{12'}$, —COOR$^{12'}$, —CONR$^{12'}$R$^{13'}$, —S(O)$_2$OR$^{12'}$, —OC(O)R$^{12'}$, —C(O)NR$^{12'}$R$^{13'}$, —NR$^{12'}$C(O)R$^{13'}$, —NR$^{12'}$SO$_2$R$^{13'}$, NR$^{12'}$C(O)NR$^{13'}$R$^{14'}$, C(NR$^{12'}$)R$^{13'}$, and —NO$_2$. R$^{12'}$, R$^{13'}$ and R$^{14'}$ are members independently selected from H, substituted or unsubstituted alkyl, substituted or unsubstituted heteroalkyl, substituted or unsubstituted aryl, and substituted or unsubstituted heteroaryl, and two or more of R$^{12'}$, R$^{13'}$, and R$^{14'}$, together with the atoms to which they are bound, are optionally joined to form a 5- to 7-membered ring system which is a member selected from substituted or unsubstituted cycloalkyl, substituted or unsubstituted heterocycloalkyl, substituted or unsubstituted aryl and substituted or unsubstituted heteroaryl, and two or more of R$^1$, R$^2$, R$^3$, R$^4$, R$^5$, R$^{12}$, R$^{11}$, R$^{13}$, R$^{14}$, R$^{12'}$, R$^{13'}$ and R$^{14'}$ are optionally joined to form a 5-7-membered ring system selected from substituted or unsubstituted cycloalkyl, substituted or unsubstituted heterocycloalkyl, substituted or unsubstituted aryl and substituted or unsubstituted heteroaryl.

In various embodiments, the invention provides a compound having a formula which is selected from:

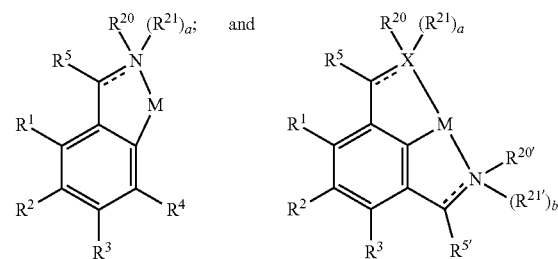

wherein, R$^{20}$, R$^{21}$, R$^{20'}$ and R$^{21'}$ are members independently selected from H, substituted or unsubstituted alkyl, substituted or unsubstituted heterocycloalkyl, substituted or unsubstituted aryl and substituted or unsubstituted heteroaryl; and a and b are selected from the integers 0 and 1, such that when a member selected from a and b is 1, the degree of unsaturation in the relevant ring including $R^{21}$ or $R^{21'}$, respectively, is not present.

In an exemplary embodiment, the invention provides a compound having the formula:

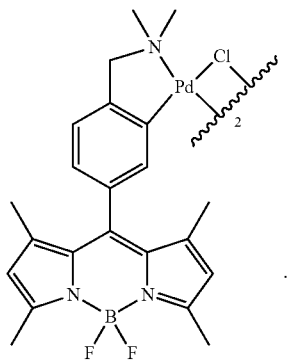

Reactive Functional Groups

Certain of the compounds of the invention bear a reactive functional group, such as a component of a linker, which can be located at any position on any aryl nucleus or on a chain, such as an alkyl chain, attached to an aryl nucleus. These compounds are referred to herein as "reactive probes." Reactive probes can be coupled to carrier species. When the reactive group is attached to an alkyl, or substituted alkyl chain tethered to an aryl nucleus, the reactive group is preferably located at a terminal position of an alkyl chain. Reactive groups and classes of reactions useful in practicing the present invention are generally those that are well known in the art of bioconjugate chemistry. Currently favored classes of reactions available with reactive probes of the invention are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups, which can be converted to esters, sulfonates, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds; and (k) phosphoramidites and other standard functional groups useful in nucleic acid synthesis.

The reactive functional groups can be chosen such that they do not participate in, or interfere with, the reactions necessary to assemble the reactive ligand. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Carrier Species

In an exemplary embodiment, a reactive functional group is utilized to attach a compound of the invention to a carrier species. A carrier species can be a targeting group Representative carrier species include, but are not limited to species that include an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a solid support, a polymeric microparticle, a biological cell, a virus and combinations thereof. In another exemplary embodiment, the carrier species is selected from a hapten, a nucleotide, an oligonucleotide, a nucleic acid polymer, a protein, a peptide or a polysaccharide. In a preferred embodiment the carrier species is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In another preferred embodiment, the carrier species is an antibody or fragment thereof, an antigen, an avidin or streptavidin, a biotin, a dextran, an antibody binding protein, a fluorescent protein, agarose, and a non-biological microparticle. Typically, the carrier species is an antibody, an antibody fragment, antibody-binding proteins, avidin, streptavidin, a toxin, a lectin, or a growth factor. Preferred haptens include biotin, digoxigenin and fluorophores.

Exemplary antibody binging proteins include protein A, protein G, soluble Fc receptor, protein L, lectins, anti-IgG, anti-IgA, anti-IgM, anti-IgD, anti-IgE or a fragment thereof.

In another exemplary embodiment, the carrier species is an amino acid (including those that are protected or are substituted by phosphates, carbohydrates, or $C_1$ to $C_{22}$ carboxylic acids), or a polymer of amino acids such as a peptide or protein. Exemplary carrier species include at least five amino acids, and preferably from 5 to 36 amino acids.

Exemplary peptides include, but are not limited to, neuropeptides, cytokines, toxins, protease substrates, and protein kinase substrates. Other exemplary peptides may function as organelle localization peptides, targeting the conjugated compound for localization within a particular cellular substructure by cellular transport mechanisms.

In another exemplary embodiment, the carrier species comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier species is a nucleoside or a deoxynucleoside or a dideoxynucleoside.

Exemplary nucleic acid polymer carrier species are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In another exemplary embodiment, the carrier species comprises a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). In a related embodiment, the polysaccharide carrier species includes dextran, agarose or FICOLL.

In another exemplary embodiment, the carrier species comprises a lipid (typically having 6-25 carbons), including glycolipids, phospholipids, and sphingolipids. Alternatively, the carrier species comprises a lipid vesicle, such as a liposome, or is a lipoprotein. Some lipophilic substituents are useful for facilitating transport of the conjugated dye into cells or cellular organelles.

Alternatively, the carrier species is a virus, cell, cellular system, cellular fragment, or subcellular particle, e.g., virus particles, bacterial particles, virus components, biological cells (such as animal cells, plant cells, bacteria, or yeast), or cellular components. Examples of cellular components that can be labeled, or whose constituent molecules can be labeled, include but are not limited to lysosomes, endosomes, cytoplasm, nuclei, histones, mitochondria, Golgi apparatus, endoplasmic reticulum and vacuoles.

In another embodiment the carrier species is a metal chelating moiety. While any chelator that binds a metal ion of interest and gives a change in its fluorescence properties is a suitable conjugate, preferred metal chelating moieties are crown ethers, including diaryldiaza crown ethers, as described in U.S. Pat. No. 5,405,975 to Kuhn et al. (1995); derivatives of 1,2-bis-(2-aminophenoxyethane)-N,N,N',N'-tetraacetic acid (BAPTA), as described in U.S. Pat. No. 5,453,517 to Kuhn et al. (1995) (incorporated by reference) and U.S. Pat. No. 5,049,673 to Tsien et al. (1991); derivatives of 2-carboxymethoxy-aniline-N,N-diacetic acid (APTRA), as described by Ragu et al., *Am. J. Physiol.,* 256: C540 (1989); and pyridyl-based and phenanthroline metal ion chelators, as described in U.S. Pat. No. 5,648,270 to Kuhn et al. (1997).

In another exemplary embodiment, the carrier species non-covalently associates with organic or inorganic materials. Exemplary embodiments of the carrier species that possess a lipophilic substituent can be used to target lipid assemblies such as biological membranes or liposomes by non-covalent incorporation of the dye compound within the membrane, e.g., for use as probes for membrane structure or for incorporation in liposomes, lipoproteins, films, plastics, lipophilic microspheres or similar materials.

The compounds of the invention can be connected to a carrier species, e.g., biomolecule, by a linker of substantially any length (zero-order or higher) and chemical composition. As such, representative linkers include, for example, substituted or unsubstituted alkyl groups, substituted heteroalkyl groups, conjugated unsaturated systems, aryl groups, heteroaryl groups, dendrimers, polyethers, polyamides, polyimines, biopolymers and linkers that are a combination of more than one of these groups. Other useful linkers will be apparent to those of skill in the art. The linker is generally attached to the compound of the invention (or its fluorescent analogue) through a linking group formed through reaction between a reactive group on the fluorogenic compound and a complementary reactive group on a linker arm precursor. The linker is attached to a carrier species through a similar reactive group. Similarly, a linking group binds the linker and carrier species.

Fluorophores and Profluorescent Moieties

The fluorogenic ("profluorescent") moiety of the compounds of the invention, when converted to the corresponding fluorescent moiety serves as a means of signal generation for assays for CO. The compounds of the invention incorporate fluorophores of substantially any structure and from substantially any source. Many appropriate fluorophore species are commercially available from, for example, the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate fluorophore for a particular application and, if it not readily available commercially, will be able to synthesize the necessary fluorophore de novo or synthetically modify commercially available fluorescent compounds to arrive at the desired fluorescent label. See, for example, Cardullo et al., *Proc. Natl. Acad. Sci. USA* 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.,* 40: 83-114 (1971); Stryer, L. *Ann. Rev. Biochem.,* 47: 819-846 (1978); Wang et al., *Tetrahedron Letters* 31: 6493-6496 (1990); Wang et al., *Anal. Chem.* 67: 1197-1203 (1995).

In an exemplary embodiment, the fluorophore is one that is capable of being quenched by a metal. Exemplary metals include Rh, Ru, Pt, Pd, Os and Ir.

In an exemplary embodiment, a profluorescent moiety and a scaffold moiety are conjugated through the reaction of reactive functional groups of complimentary reactivity to form the compounds of the invention. Techniques standard in the art of synthetic organic chemistry are appropriate for assembling the compounds of the invention.

In addition to small molecule fluorophores, naturally occurring fluorescent proteins and engineered analogues of such proteins are useful with the fluorogenic species of the present invention. Such proteins include, for example, green fluorescent proteins of cnidarians (Ward et al., *Photochem. Photobiol.* 35:803-808 (1982); Levine et al., *Comp. Biochem. Physiol.,* 72B:77-85 (1982)), yellow fluorescent protein from Vibrio fischeri strain (Baldwin et al., *Biochemistry* 29:5509-15 (1990)), Peridinin-chlorophyll from the dinoflagellate *Symbiodinium* sp. (Morris et al., *Plant Molecular Biology* 24:673:77 (1994)), phycobiliproteins from marine cyanobacteria, such as *Synechococcus*, e.g., phycoerythrin and phycocyanin (Wilbanks et al., *J. Biol. Chem.* 268:1226-35 (1993)), and the like.

A non-limiting list of exemplary fluorophores that are of use in the compounds of the invention is provided in Table 1.

TABLE 1

Exemplary Fluorophores 4-acetamido-4'-isothiocyanatostilbene-2,2'disulfonic acid
acridine and derivatives:
    acridine
    acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:
coumarin
    7-amino-4-methylcoumarin (AMC, Coumarin 120)
    7-amino-4-trifluoromethylcouluarin (Coumaran 151)
cyanine dyes
cyanosine
4',6-diaminidino-2-phenylindole (DAPI)
5',5''-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:
erythrosin and derivatives:
    erythrosin B
    erythrosin isothiocyanate
ethidium
fluorescein and derivatives:
    5-carboxyfluorescein (FAM)
    5-(4,6-dichlorotriazin-2-yl)aminofluorescein (DTAF)
    2',7'-dimethoxy-4'5'-dichloro-6-carboxyfluorescein (JOE)
    fluorescein
    fluorescein isothiocyanate
    QFITC (XRITC)
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde
pyrene and derivatives:
    pyrene
    pyrene butyrate
    succinimidyl 1-pyrene butyrate
quantum dots
Reactive Red 4 (Cibacron ™ Brilliant Red 3B-A)
rhodamine and derivatives:
    6-carboxy-X-rhodamine (ROX)
    6-carboxyrhodamine (R6G)
    lissamine rhodamine B sulfonyl chloride rhodamine (Rhod)
    rhodamine B
    rhodamine 123
rhodamine X isothiocyanate
    sulforhodamine B
    sulforhodamine 101
sulfonyl chloride derivative of sulforhodamine 101 (Texas Red)
N,N,N',N'-tetramethyl-6-carboxyrhodamine (TAMRA)
tetramethyl rhodamine
    tetramethyl rhodamine isothiocyanate (TRITC)
riboflavin
rosolic acid
lanthanide chelate derivatives Exemplary fluorophores of use in the compounds of the invention include, without limitation, derivatives of fluorescein, rhodamine, rhodols, cyanines, and naphthalenes.

Additional fluorophores include derivatives of:

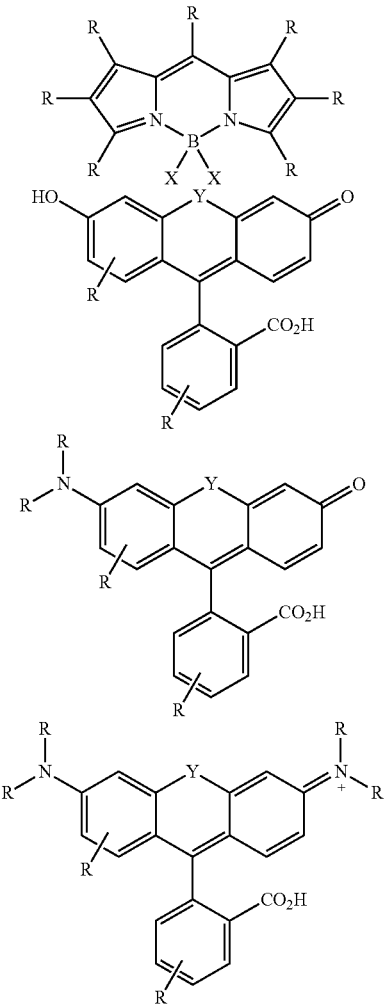

in which R can be any aryl substituent group as that term is defined herein, located at any position on the fluorophore scaffold. Each X is an independently selected substituent on the BODIPY boron such as F, or MeO. Y is a heteroatom, e.g., oxygen or nitrogen or silicon with R groups.

In an exemplary embodiment, the fluorophore is a BODIPY species. Exemplary BODIPY species of use in the invention include:

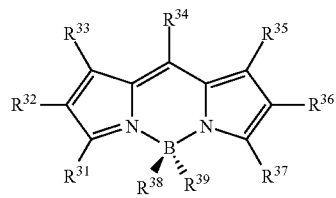

wherein $R^{31}$, $R^{32}$, $R^{33}$, $R^{34}$, $R^{35}$, $R^{36}$ and $R^{37}$ are members independently selected from H, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein at least one of $R^{31}$, $R^{32}$, $R^{33}$, $R^{34}$, $R^{35}$, $R^{36}$ and $R^{37}$ comprises a bond to the remainder of the compound according to Formula I. $R^{38}$ and $R^{39}$ are members independently selected from H, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, and $NR^{40}R^{41}$. $R^{40}$ and $R^{41}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

Various BODIPY structures of use in the invention include:

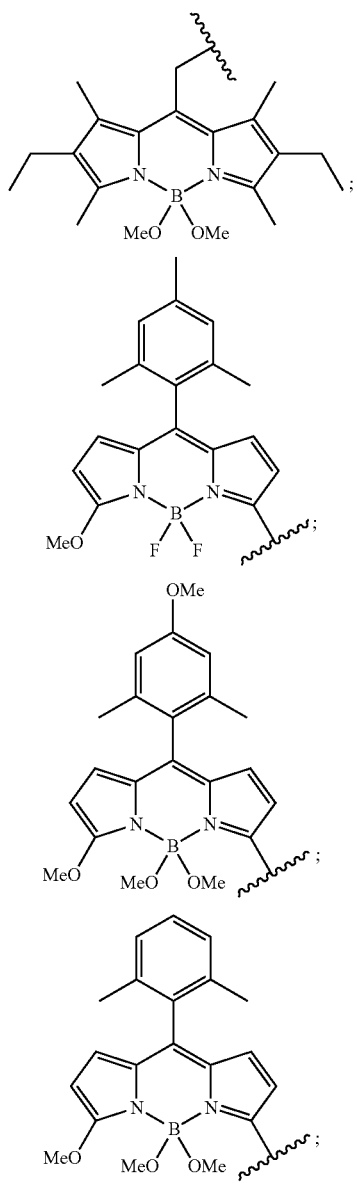

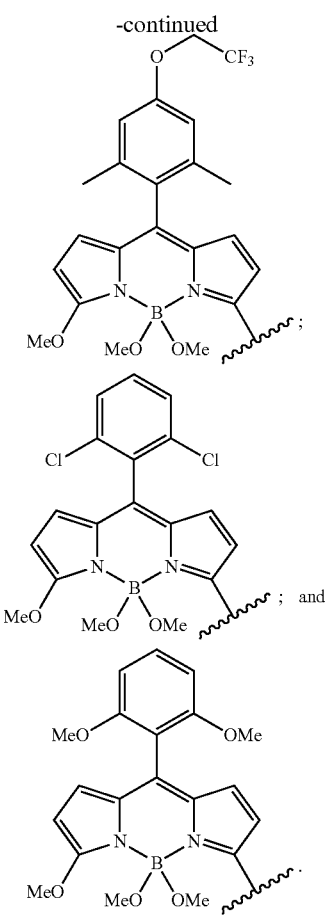

There is a great deal of practical guidance available in the literature for selecting appropriate fluorophores for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties, for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via readily available reactive groups on the fluorophore, quencher and on molecular scaffolds functionalizable with either or both these species.

The diversity and utility of chemistries available for conjugating fluorophores and quenchers to other molecules and surfaces is exemplified by the extensive body of literature on preparing nucleic acids derivatized with fluorophores. See, for example, Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a small molecular bioactive material, nucleic acid, peptide or other polymer.

In an exemplary embodiment, the metal, M, and the fluorophore are selected such that they form an energy transfer pair. Thus, in this embodiment, the metal is able to absorb the fluorescence emission from the fluorophore donor. One factor to be considered in choosing the fluorophore-quencher pair is the efficiency of energy transfer between them. Preferably, the efficiency of energy transfer between the fluorophore and metal is at least 10%, more preferably at least 50% and even more preferably at least 80%. The efficiency of energy transfer can easily be empirically tested using the methods both described herein and known in the art.

In addition to fluorophores that are attached directly to a probe, the fluorophores can also be attached by indirect means. In this embodiment, a ligand molecule (e.g., biotin) is preferably covalently bound to the probe species. The ligand then binds to another molecules (e.g., streptavidin) molecule, which is either inherently detectable or covalently bound to a signal system, such as a fluorescent compound of the invention, or an enzyme that produces a fluorescent compound by conversion of a non-fluorescent compound. Useful enzymes of interest as labels include, for example, CO generating or CO degrading enzymes.

The fluorphores and an appropriate donor or acceptor moiety can be attached to a carrier species using any methodology known in the art. Representative methods include those relevant to preparing fluorescently labeled nucleic acids. See, for example: Eckstein, editor, Nucleic Acids and Analogues: A Practical Approach (IRL Press, Oxford, 1991); Zuckerman et al., *Nucleic Acids Research,* 15: 5305-5321 (1987) (3'-thiol group on nucleic acid); Sharma et al., *Nucleic Acids Research,* 19: 3019 (1991) (3'-sulfhydryl); Giusti et al., *PCR Methods and Applications,* 2: 223-227 (1993) and Fung et al., U.S. Pat. No. 4,757,141 (5'-phosphoamino group via Aminolink TM II available from P.E. Biosystems, CA.) Stabinsky, U.S. Pat. No. 4,739,044 (3-aminoalkylphosphoryl group); Agrawal et al., *Tetrahedron Letters,* 31: 1543-1546 (1990) (attachment via phosphoramidate linkages); Sproat et al., *Nucleic Acids Research,* 15: 4837 (1987) (5-mercapto group); Nelson et al., *Nucleic Acids Research,* 17: 7187-7194 (1989) (3'-amino group), and the like.

The Methods

Assays

The following discussion is generally relevant to the assays described herein. This discussion is intended to illustrate the invention by reference to certain preferred embodiments and should not be interpreted as limiting the scope of probes and assay types in which the compounds of the invention find use. Other assay formats utilizing the compounds of the invention will be apparent to those of skill in the art.

Assays based on specific binding reactions are used for detecting a wide variety of substances such as drugs, hormones, enzymes, proteins, antibodies, and infectious agents in various biological fluids and tissue samples. In general, the assays consist of an analyte, a recognition moiety for the analyte, and a detectable label. Competitive assay modalities generally utilize a binding partner in addition to these components. In an exemplary embodiment, the binding partner is a molecule that interacts with a recognition moiety to form a complex that is inherently less stable than a similar complex formed between the recognition moiety and the analyte, and is subsequently displaced by the incoming analyte.

Because the results of specific binding interactions are frequently not directly observable, a variety of fluorescent labels have been devised for determining the presence of an interaction. The fluorophores of the invention are detected by use of fluorescence spectroscopy or by the naked eye. An introduction to labels, labeling procedures and detection of labels, such as are useful in practicing the present invention, is found in Polak et al., INTRODUCTION TO IMMUNOCYTOCHEMISTRY, 2nd Ed., Springer Verlag, NY, (1977), and in Haugland, HANDBOOK OF FLUORESCENT PROBES AND RESEARCH CHEMICALS, a combined handbook and catalogue Published by Molecular Probes, Inc., Eugene, Oreg. (1996).

In various embodiments, the invention provides a method of detecting the presence of CO in a cell, the method comprising: (a) contacting the cell with the fluorogenic compound according to the invention, under conditions appropriate to convert the compound to a fluorescent compound upon its carboylation by the CO; b) exciting the fluorescent compound; and (c) determining a fluorescence property of the fluorescent compound, wherein the presence of CO in the sample results in a fluorescence property of the fluorescent compound which is different from the fluorescence property in the fluorogenic compound.

In certain embodiments, the assay is a competitive assay, e.g., $O_2$ and CO at the iron site of hemoglobin.

In various embodiments, the invention provides a method for determining whether a compound alters an activity of an enzyme, the method comprising: (a) contacting the enzyme with a fluorogenic compound according to the invention, under conditions appropriate to convert the compound to a fluorescent compound upon its carboylation by the CO; (b) exciting the fluorescent compound; and (c) determining a fluorescence property of the fluorescent compound, wherein the presence of CO in the sample results in a fluorescence property of the fluorescent compound which is different from the fluorescence property in the fluorogenic compound.

In a competitive assay format, one or more than one of the components is labeled with a compound of the invention. a component of the assay is labeled with a compound of the invention and CO binding or release is detected by the appearance or disappearance of fluorescence or in a liquid phase of the assay. This embodiment is offered by way of example only and it will be plain to one of skill in the art that many other competitive assay formats can utilize and benefit from the compounds of the invention.

In addition to ascertaining a binding event, it is frequently desired to quantitate the magnitude of the affinity between two or more binding partners. Thus, it is also within the scope of the present invention to utilize the compounds disclosed herein as a support for such assays.

Most typically, the amount of CO present is measured by quantitating the amount of fluorescence in a sample containing a compound of the invention. Means of detecting and quantitating fluorescent labels are well known to those of skill in the art.

The format of an assay for extracting affinity data for two molecules can be understood by reference to an embodiment in which a ligand that is known to bind to a receptor is displaced by an antagonist to that receptor. Other variations on this format will be apparent to those of skill in the art. The competitive format is well known to those of skill in the art. See, for example, U.S. Pat. Nos. 3,654,090 and 3,850,752.

In a further aspect, there is provided a method for determining the presence or absence of CO in a sample. The method includes: a) contacting the sample with a compound of the invention; b) incubating the sample for a sufficient amount of time to allow the CO to react with the fluorogenic compound to produce a fluorescent product; c) illuminating the sample from b) with light of an appropriate wavelength;

and d) observing the presence or absence of fluorescence from the sample, whereby the presence or absence of CO in the sample is determined.

In other embodiments, the compounds of the invention are utilized to stain a sample to give a detectable optical response under desired conditions by first preparing a solution comprising a compound of the invention, at a concentration sufficient to yield a detectable optical response under the desired conditions. Specifically the methods for staining a sample include: a) contacting the sample with a compound of the invention; b) incubating the labeled sample for a sufficient amount of time to allow reaction between the compound and CO; c) illuminating the sample from b) with light of an appropriate wavelength to excite the fluorophore; and d) detecting fluorescence in the sample.

For example, a compound of the invention is used to monitor CO in the sample with respect to its spatial and temporal distribution in the sample.

In one embodiment, the compounds of the present invention are cell permeant, and can be introduced into the sample cell or cells by incubation of the cell or cells in a solution containing the compounds. Any other method of introducing the compound into the sample cell, such as microinjection of a solution of the compound of the invention, scrape loading techniques (short mechanical disruption of the plasma membrane where the plasma membrane is peeled away from the cytoplasm, the compound of the invention is perfused through the sample and the plasma membrane reassembled), or patch clamp methods (where an opening is maintained in the plasma membrane for long periods) can be used. Any other treatment that will permeabilize the plasma membrane, such as electroporation, shock treatments or high extracellular ATP can be used to accelerate introduction of the fluorogen into the cellular cytoplasm. Microinjection of a solution of the compound of the invention is of particular use when analysis of a single cell is desired, within a colony of other sample cells.

In various embodiments, the compounds of the invention are utilized as an aid to understanding the role(s) of CO in cellular signalling. In an exemplary embodiment, the compounds and methods are utilized in methods to assay the levels of CO in live cell systems, which can be applied to a variety of physiological and pathophysiological states that are relevant to human health.

A typical experiment involves the application of COP-1 (1 µM) to a monolayer of cells in DPBS buffer. The cells would be allowed to incubate with the probe for 30 minutes at 37° C., and then a specific amount of CORM-3 (1-100 µM) would be added to the media and incubated with the cells for a given time (30-45 min) at which point the cells would be visualized by fluorescence microscopy and compared to a vehicle control culture of cells. In an exemplary embodiment, the compound of the invention is of use to look at cells (that may represent a disease state) where levels of the CO producing enzymes heme oxygenases (HO) are known to be present at higher levels. The compounds of the invention can also be used to investigate the role of CO in cellular studies for the exogenous addition of various CORM molecules and the resulting cellular responses. The compounds of the invention can also be used to monitor CO levels in aqueous or organic solutions.

Further, the compounds of the invention can be utilized in live cells, e.g., HEK293T cells to determine if the inherent chemistry that we were looking to use would be compatible with the complex intracellular environment. An exemplary experiment yields very little background fluorescence in vehicle control experiments, and a dose dependent increase in fluorescence.

In an exemplary embodiment, the compounds of the invention are substantially non-toxic to cells in the amounts that the compounds are used to detect CO in the cells.

Multiplex Analyses

The compounds of the invention fluoresce at a number of distinct wavelength ranges, providing fluorophores of different colors. Thus, the compounds of the invention are of use as detectable probes in an assay for detecting multiple species in a sample or, alternatively, the same species (e.g., CO) in multiple compartments. An assay used to detect two or more species by using at least two probes bearing different fluorophores is referred to herein as a "multiplex analysis."

Compounds of the invention are also useful in performing multiplex-type analyses and assays. In a typical multiplex analysis, two or more distinct species (or regions containing one or more species) are detected using two or more compounds of the invention. Preferred multiplex analyses relying on fluorescence ideally meet several criteria. The fluorescent species should be bright and spectrally well-resolved and the energy transfer between the fluorescent species and the acceptor should be efficient.

The compounds of the present invention can be used in multiplex assays designed to detect and/or quantify substantially any sample that includes CO, generates or degrades CO, or binds to or releases CO, including, for example, whole cells, viruses, proteins (e.g., enzymes, antibodies, receptors), glycoproteins, lipoproteins, subcellular particles, organisms (e.g., *Salmonella*), nucleic acids (e.g., DNA, RNA, and analogues thereof), polysaccharides, lipopolysaccharides, lipids, fatty acids, non-biological polymers and small bioactive molecules (e.g., toxins, drugs, pesticides, metabolites, hormones, alkaloids, steroids).

Sample Preparation

The end user will determine the choice of the sample and the way in which the sample is prepared. The sample includes, without limitation, any biological derived material or aqueous solution that is thought to contain a target analyte.

The sample can be a biological fluid such as whole blood, plasma, serum, nasal secretions, sputum, saliva, urine, sweat, transdermal exudates, cerebrospinal fluid, or the like. Biological fluids also include tissue and cell culture medium wherein an analyte of interest has been secreted into the medium. Alternatively, the sample may be whole organs, tissue or cells from the animal. Examples of sources of such samples include muscle, eye, skin, gonads, lymph nodes, heart, brain, lung, liver, kidney, spleen, thymus, pancreas, solid tumors, macrophages, mammary glands, mesothelium, and the like. Cells include without limitation prokaryotic cells and eukaryotic cells that include primary cultures and immortalized cell lines. Eukaryotic cells include without limitation ovary cells, epithelial cells, circulating immune cells, beta-cells, hepatocytes, and neurons.

Various buffers may be used that do not interfere with the generation of a fluorescent signal by conversion of the fluorogen. These buffers include PBS, Tris, MOPS, HEPES, phosphate, etc. The pH will vary depending upon the particular monooxygenase being assayed, generally being in the range of about 7.0-7.5

Kits

In another aspect, the present invention provides kits that include a fluorogenic or fluorescent compound of the invention. The kit will generally also include instructions for using the compound of the invention in one or more methods.

In an exemplary embodiment, the kit includes a compound of the invention and instructions for detecting CO in an assay mixture or in a cell.

The kit optionally further contains buffers and/or reagents for a CO detection experiment.

Microarrays

The invention also provides microarrays including immobilized compounds of the invention. Moreover, the invention provides methods of interrogating microarrays using probes that are functionalized with fluorogenic species. The immobilized species and the probes are selected from substantially any type of molecule, including, but not limited to, small molecules, peptides, enzymes nucleic acids and the like.

Nucleic acid microarrays consisting of a multitude of immobilized nucleic acids are revolutionary tools for the generation of genomic information, see, Debouck et al., in supplement to Nature Genetics, 21:48-50 (1999). The discussion that follows focuses on the use of fluorogenic species in conjunction with nucleic acid microarrays. This focus is intended to be illustrative and does not limit the scope of materials with which this aspect of the present invention can be practiced.

Thus, in another preferred embodiment, the compounds of the present invention are utilized in a microarray format. The fluorogenic compounds, or carrier species bearing fluorogenic species can themselves be components of a microarray or, alternatively they can be utilized as a tool to screen components of a microarray.

In an exemplary embodiment, the present invention provides a method of screening a microarray. The method includes contacting the members of the microarray with a compound of the invention and interrogating the microarray for regions of fluorescence. The fluorescent regions are indicative of the presence of an interaction between the compound and CO. In another version of this method, the microarray is interrogated for regions in which fluorescence is quenched, indicating the absence of an interaction between the compound of the invention and CO.

In an exemplary embodiment, the microarrays comprise n regions with n compounds of the invention. The compounds can be the same or different. In various embodiments, n is a number from 2 to 100, more preferably, from 10 to 1,000, and more preferably from 100 to 10,000. In a still further preferred embodiment, the n probes are patterned on a substrate as n distinct locations in a manner that allows the identity of each of the n locations to be ascertained.

In yet another preferred embodiment, the invention also provides a method for preparing a microarray of n compounds of the invention. The method includes attaching compounds of the invention to selected regions of a substrate. A variety of methods are currently available for making arrays of molecules. The following examples are offered to illustrate selected embodiments of the invention and not to define or limit the scope of the present invention.

The following non-limiting examples are provided to illustrate certain embodiments of the invention.

EXAMPLES

Example 1

General Methods

All reactions utilizing air- or moisture-sensitive reagents were performed in dried glassware under an atmosphere of dry $N_2$. When dry solvent was used the solvent was passed over activated alumina. Other reagents were used without further purification. Silica gel P60 (SiliCycle) was used for column chromatography and SiliCycle 60 F254 silica gel (precoated sheets, 0.25 mm thick) was used for analytical thin layer chromatography and visualized by fluorescence quenching under UV light. Ruthenium hexacarbonyldi-µ-chlorodimer was purchased from Strem, 4-(chloromethyl)benzoyl chloride was purchased from TCI America, carbon monoxide gas was purchased from Praxair, and all other reagents were purchased from Sigma-Aldrich. CORM-3 [Ru(CO)$_3$(glycinate)] was prepared according to the literature procedure and spectral properties were in accordance with those reported (Clark, J. E.; Naughton, P.; Shurey, S.; Green, C. J.; Johnson, T. R.; Mann, B. E.; Foresti, R.; Motterlini, R. Circulation Research 2003, 93, e2-e8). $^1$H and $^{13}$C NMR spectra for characterization of new compounds were collected in CDCl$_3$ (Cambridge Isotope Laboratories) at 25° C. at the reported frequency at the College of Chemistry NMR Facility at the University of California, Berkeley. All chemical shifts are reported in parts per million and referenced to the residual solvent peak from CHCl$_3$ at 7.27 ppm. Splitting patterns are indicated as follows: br, broad; s, singlet; d, doublet; t, triplet; q, quartet; m, multiplet; dd, doublet of doublets; dt, doublet of triplets. Low-resolution mass spectral analyses were carried out using a LC-MS (Agilent Technology 6130, Quadrupole LC/MS). Fluorescence spectra were obtained using a Quanta Master 4 L-format scanning spectrofluorometer equipped with an LPS-220B 75 W xenon lamp and power supply, A-1010B lamp housing with an integrated igniter, switchable 814 photon-counting/analog photomultiplier detection unit, and MD5020 motor driver (Photon Technology International, Inc.) and UV spectra were acquired using a Cary Bio50 UV spectrophotometer (Varian). Samples for emission and absorption measurements were contained in 1 cm×0.1 cm quartz cuvette (Starna).

Probe Synthesis and New Compound Characterization
Compound 2:

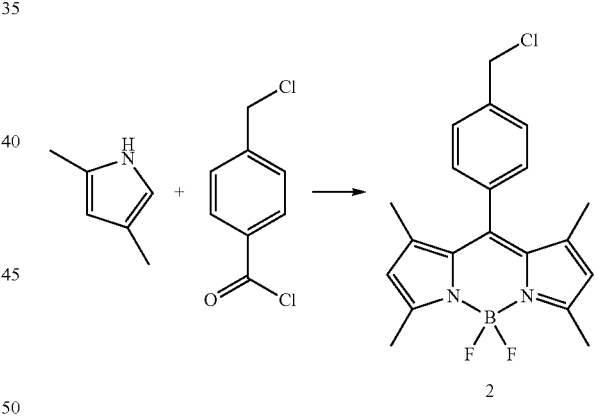

To an oven dried 250 mL 3-necked round bottomed flask with a magnetic stir bar and equipped with a water cooled condenser was charged dry CH$_2$Cl$_2$ (100 mL) followed by 2,4-dimethylpyrrole (3.12 mL, 30.3 mmol, 2.1 equiv.). Under flow of nitrogen, 4-(chloromethyl)benzoyl chloride (2.864 g, 14.36 mmol, 1.0 equiv.) was added in approximately 200 mg portions. The mixture was then heated in an oil bath at 50° C. for 80 min and then subsequently allowed to cool to room temperature. The solution was transferred to an oven dried 500 mL round bottomed flask and the majority of solvent was removed in vacuo until 10-15 mL of CH$_2$Cl$_2$ remained. Dry toluene (180 mL) was then added to the flask and the solution was put under an atmosphere of nitrogen. Dry triethylamine (8.5 mL) was charged to the flask and the mixture was allowed to stir at room temperature for 15 min, at which point BF$_3$.Et$_2$O (9.5 mL) was added to the flask in a dropwise fashion. The flask was then equipped with a water cooled condenser and heated to 50° C. for 1 h. The mixture was then allowed to cool to room temperature and the solvent was removed in vacuo. The resulting residue was dissolved in $CH_2Cl_2$ (100 mL) and transferred to a separatory funnel. The organic layer was washed with water (3×50 mL) and then dried over $Na_2SO_4$, filtered and concentrated. The residue was dry loaded onto 75 mL of silica and subsequently purified by flash chromatography on silica gel $CH_2Cl_2$:Hexanes (50:50→60:40→75:25) to provide 2 (1.47 g, 3.95 mmol) as an orange solid in 27% yield. $^1$H NMR (400 MHz, $CDCl_3$) δ 7.53 (d, J=8.0 Hz, 2H), 7.29 (d, J=8.0 Hz, 2H), 5.99 (s, 2H), 4.57 (s, 2H), 2.56 (s, 6H), 1.38 (s, 6H). $^{13}$C NMR (100 MHz, $CDCl_3$) δ 155.8, 143.2, 141.1, 138.8, 135.2, 131.5, 129.4, 128.6, 121.5, 45.8, 14.8, 14.7. HRMS calcd for $C_{20}H_{21}BClF_2N_2$ (M+H$^+$) 373.1449. found 373.1440.

Compound 3:

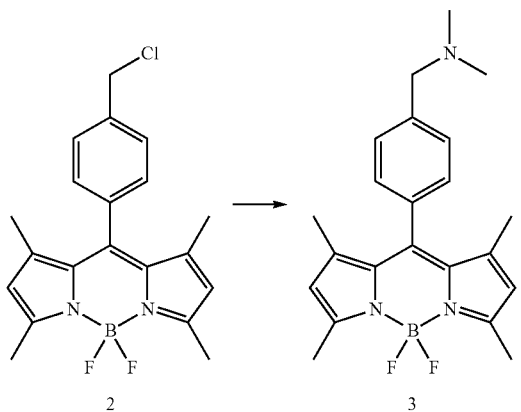

To a 10 mL microwave vial (CEM corp.) was weighed 2 (376 mg, 1.01 mmol, 1.0 equiv.), $K_2CO_3$ (276 mg, 2.0 mmol, 2.0 equiv.), and KI (336 mg, 2.02 mmol, 2.0 equiv.). A magnetic stir bar was added and the vial was subsequently charged with $CH_3CN$ (5.0 mL) and $Me_2NH$ (2.3 mL aq. 40 wt %, 20 mmol, 20 equiv.). The microwave vial cap was affixed onto the vial and the reaction mixture was heated at 80° C. (100 W) for 40 min followed by 20 min at 100° C. After the vessel was cooled back to room temperature the mixture was diluted with $CH_2Cl_2$ (60 mL), transferred to a separatory funnel and washed with water (2×30 mL) and Brine (1×45 mL). The organic phase was dried over $Na_2SO_4$, filtered and concentrated in vacuo. The resulting residue was purified by flash chromatography eluting with $CHCl_3$→66% $CHCl_3$, 30% ethyl acetate, 3% methanol, 0.5% triethylamine→45% $CHCl_3$, 45% ethyl acetate, 9% methanol, 1% triethylamine. The fractions containing pure product as indicated by fluorescence visualization of TLC were combined and concentrated to provide 3 (326 mg, 0.855 mmol) as an orange solid in 85% yield. $^1$H NMR (400 MHz, $CDCl_3$): δ 7.43 (d, J=7.9 Hz, 2H), 7.24 (d, J=7.9 Hz, 2H), 5.98 (s, 2H), 3.50 (s, 2H), 2.55 (s, 6H), 2.26 (s, 6H), 1.39 (s, 6H). $^{13}$C NMR (100 MHz, $CDCl_3$) δ 155.53, 143.27, 141.95, 139.96, 133.98, 131.66, 130.15, 128.06, 121.36, 64.25, 45.45, 14.78, 14.54. HRMS calcd for $C_{22}H_{27}BF_2N_3$ (M+H$^+$) 382.2261. found 382.2258.

COP-1:

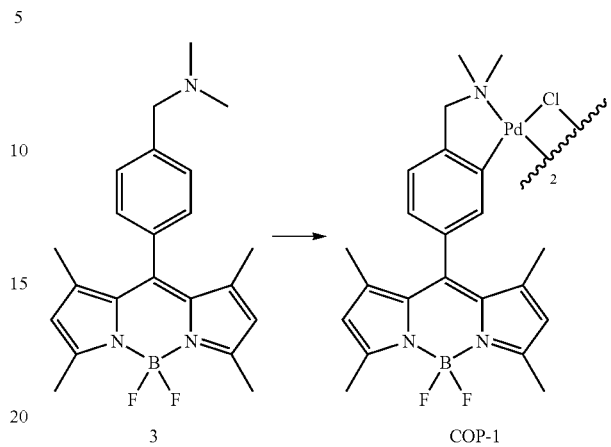

To a 20 mL vial was weighed 3 (254 mg, 0.667 mmol, 1.05 equiv.) and $Pd(OAc)_2$ (143 mg, 0.636 mmol, 1.00 equiv.). A magnetic stir bar was added to the vial along with benzene (12 mL). The mixture was sonicated for 1 minute, then nitrogen atmosphere was established. The vial was then wrapped in foil to protect from light and placed in a 50° C. oil bath and the mixture was stirred for 14 h. The reaction mixture was then cooled to room temperature and hexanes (6 mL) was added which caused an immediate precipitation of an orange solid. The solid was collected via filtration to provide the acetate bridged dimer (340 mg) that co-crystallized with one benzene relative to two dimers (1 benzene: 4 Pd-complex). Some of this material was retained for evaluation and the remaining (264 mg, 0.483 mmol) was dissolved in acetone that had been saturated with LiCl. This mixture was stirred at room temperature protected from light for 4 h, at which point the solvent was removed in vacuo and the residue was dissolved in $CH_2Cl_2$ (20 mL) and passed through a pad of celite. The pad of celite was further washed with $CH_2Cl_2$ (75 mL) and the combined eluent was concentrated in vacuo to provide the chloride dimer COP-1 (251 mg, 0.481 mmol) as an orange solid in 97% yield over both steps. The $^1$H NMR spectrum indicates that the dimer exist as a mixture of isomers which coalesce upon heating of the sample. While we hypothesize that the isomers are rotomers about the BODIPY-Aryl bond, it is difficult to assign the predominant solution structure. Therefore, the reported peaks correspond to the predominant isomer. $^1$H NMR (400 MHz, $CDCl_3$) δ 7.04 (s, 1H), 6.98 (d, J=7.6 Hz, 1H), 6.88 (d, J=7.5 Hz, 1H), 5.98 (s, 2H), 3.98 (s, 2H), 2.85 (s, 6H), 2.55 (s, 6H), 1.47 (s, 6H). $^{13}$C NMR (100 MHz, $CDCl_3$) δ 155.1. 147.8, 144.2, 143.6, 143.0, 131.9, 131.7, 131.2, 124.2, 122.0, 121.1, 73.2, 53.1, 14.76. Elemental Analysis calcd for $C_{44}H_{50}B_2Cl_2F_4N_6Pd_2$: C, 50.61; H, 4.83; N, 8.05. Found: C, 50.64; H, 5.01; N, 7.80.

Compound 4:

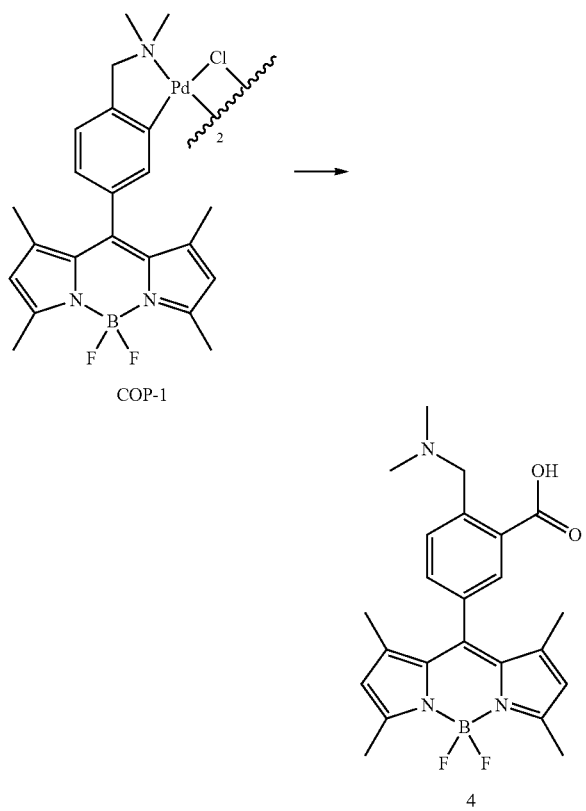

Figure 8:
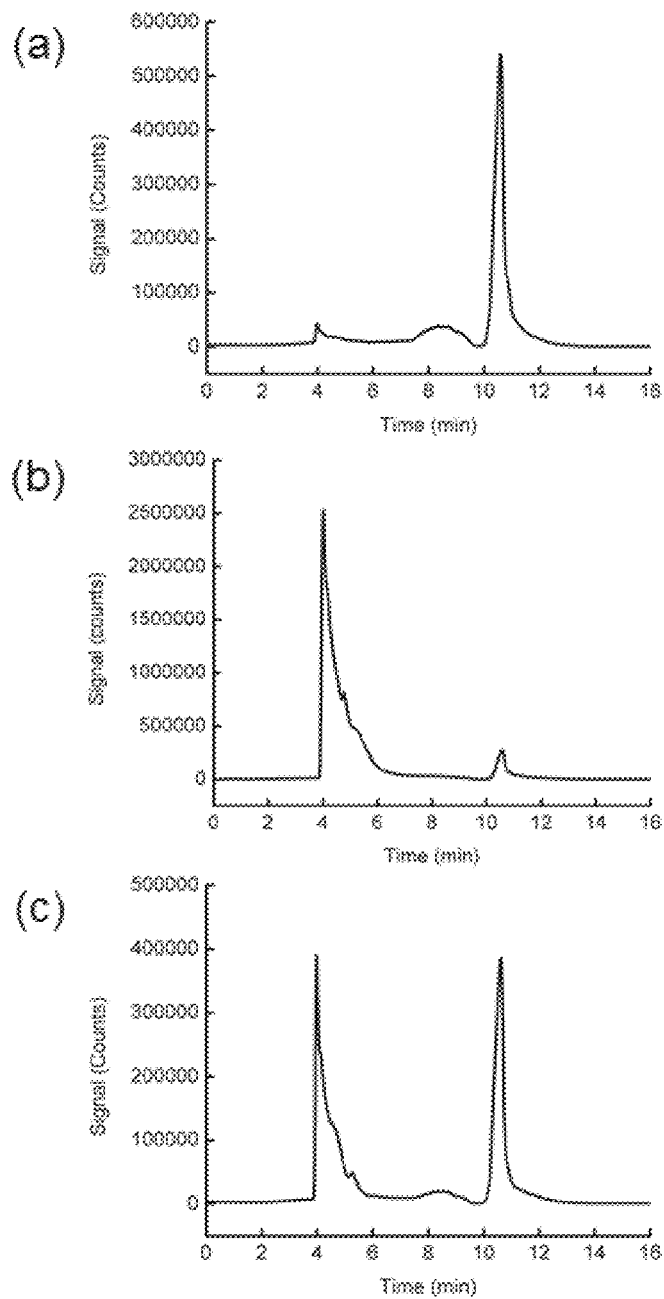
FIG. 8A-8C show HPLC-MS traces in scanning ion mode (4+H, m/z=426; COP-1-$(CH_3CN)_2$, m/z=568). HPLC conditions: Gradient from 80% water, 20% $CH_3CN$ to 100% $CH_3CN$ over 8 min using an Agilent 300 extend-C18, 3.5 µm, 4.6×100 mm column. (a) COP-1 dissolved in acetonitrile; (b) Compound 4; (c) A reaction was performed with 10 µM COP-1 in 100 mL of $H_2O$ under an atmosphere of CO gas and at 37° C.

To a 50 mL round bottomed flask was weighed COP-1 (35.0 mg, 0.067 mmol). A magnetic stir bar was added along with $CH_2Cl_2$ (15 mL) and water (0.5 mL). The flask was fitted with an air condenser and an atmosphere of CO was established via flushing the apparatus from a balloon of CO. The mixture was heated in an oil bath at 31 C overnight (14 h) while maintaining an atmosphere of CO. The reaction mixture was cooled to room temperature, transferred to a separatory funnel and diluted with $CH_2Cl_2$ (50 mL). The solution was washed with water (1×20 mL), dried over $Na_2SO_4$, filtered and concentrated. The crude product was purified by flash chromatography by eluting with a copious amount of a mixed solvent (~1.5 L) of methanol in $CHCl_3$ (6%→12%→15% methanol). The product containing fractions were concentrated and when transferring to a vial the residue was dissolved in $CHCl_3$ and passed through a short plug of celite in a pipette to remove any residual silica. The product 4 (27.3 mg, 0.064 mmol) was isolated as an orange solid in 96% yield. $^1$H NMR (400 MHz, $CDCl_3$): δ 8.14 (s, 1H), 7.39 (d, J=7.7 Hz, 1H), 7.35 (d, J=7.7 Hz, 1H), 5.98 (s, 2H), 3.98 (s, 2H), 2.57 (s, 6H), 2.55 (s, 6H), 1.37 (s, 6H). $^{13}$C NMR (100 MHz, $CDCl_3$): 174.8, 156.2, 142.8, 139.8, 136.7, 133.4, 132.7, 131.9, 131.3, 130.9, 121.7, 62.4, 42.5, 14.9, 14.8. MS calcd for $C_{23}H_{27}BF_2N_3O_2$ $(M+H^+)$ 426.2159. found 426.2157. For in vitro evaluations of the carbonylation reaction with CO gas (1 atm) the identity of the product formed from COP-1 was confirmed to be the acid 4 via comparison of LC-MS for the observed and authentic product (FIG. 8).

Quantum Yields

Quantum yields were determined according to the literature procedure using fluorescein as the standard. Absorption and emission spectra for COP-1, the carbonylation product 4, and fluorescein were obtained over a range of concentrations (100 nM to 10 uM) where a linear correlation between concentration and absorption was observed and the absorbance was within 0.01 to 0.1. The quantum yield was calculated according to the equation $\Phi_{sample}=\Phi_{standard}(Grad_{sample}/Gad_{standard})(\eta_{sample}/\eta_{standard})$; where Φ is quantum yield, $\Phi_{standard}$=0.925 in 0.1 M NaOH, Grad is the slope of the plot of absorbance versus integrated emission intensity, and θ is the refractive index of the solvent.

COP-1 Fluorescence Responses to CO

A 1.0 μM solution of COP-1 in DPBS (—Ca, —Mg) buffer was prepared in a cuvette from a 500 μM stock solution of COP-1 in DMSO. The cuvette was placed in a water bath set to 37° C. A t=0 spectrum was acquired and 10 μL of a 5 mM stock solution of CORM-3 in Millipore water was added to the cuvette to bring the concentration of the CORM-3 in solution to 50 nM. Emission spectra were recorded by quickly removing the cuvette from the water bath, obtaining the spectrum and returning the cuvette to the bath. Spectra were taken at t=0, 5, 15, 30, 45, and 60 mM. See FIG. 2. For in vitro evaluations of the carbonylation reaction with either CORM-3 or CO gas (1 atm) the identity of the product formed from COP-1 was confirmed to be the acid 4 via comparison of LC-MS for the observed and authentic product.

A 1.0 μM solution of COP-1 in DPBS (—Ca, —Mg) buffer was prepared in a cuvette from a 500 μM stock solution of COP-1 in DMSO. The cuvette was placed in a water bath set to 37° C. A t=0 spectrum was acquired then CORM-3 was added from a 5 mM stock solution in Millipore water was added to the cuvette to bring the solution to the desired concentration of CORM-3. Emission spectra were recorded by quickly removing the cuvette from the water bath, obtaining the spectrum and returning the cuvette to the bath. Spectra were taken at t=0, 5, 15, 30, 45, and 60 min.

Selectivity Tests

A 1.0 μM solution of COP-1 in DPBS (—Ca, —Mg) buffer was prepared in a cuvette from a 500 μM stock solution of COP-1 in DMSO. The cuvette was placed in a water bath set to 37° C. A t=0 spectrum was acquired then the analyte of interest was added to the vial to bring the concentration of analyte to 50 μM. Emission spectra were recorded by quickly removing the cuvette from the water bath, obtaining the spectrum and returning the cuvette to the bath. Spectra were taken at t=0, 5, 15, 30, 45, and 60 min. See FIG. 2B.

$H_2O_2$: 5 μL of 10 mM stock solution of $H_2O_2$ in Millipore water was added to 995 μL of 1.0 μM solution of COP-1 in DPBS.

TBHP: 5 μL of 10 mM stock solution of TBHP in Millipore water was added to 995 μL of 1.0 μM solution of COP-1 in DPBS.

NaOCl: 5 μL of 10 mM stock solution of NaOCl in Millipore water was added to 995 μL of 1.0 μM solution of COP-1 in DPBS.

$O_2^{•-}$: 5 μL of ~10 mM saturated solution of $KO_2$ in Millipore water was added to 995 μL of 1.0 μM solution of COP-1 in DPBS.

NO: 3.85 μL of 6.5 mM Prolin-NONOATE (13 mM NO equiv.) was added to 996 μL of 1.0 μM solution of COP-1 in DPBS. Note: All solutions degassed prior to reaction.

$ONOO^-$: 0.56 μL of 89 mM $ONOO^-$ solution in Millipore water was added to 999 μL of 1.0 μM solution of COP-1 in DPBS.

$H_2S$: 5 μL of a 10 mM $Na_2S$ solution in Millipore water was added to 995 μL of 1.0 μM solution of COP-1 in DPBS.

Cell Culture and Labeling Procedures

HEK 293T cells were maintained in exponential growth as a monolayer in Dulbecco's Modified Eagle Mediaum (DMEM, Invitrogen) supplemented with 10% fetal bovine serum (FBS, Hyclone), and incubated at 37° C. in 5% $CO_2$. One or two days before imaging, the cells were passaged and plated in phenol red-free medium on a 4-well Lab Tek borosilicate chambered cogerglass slides (Nunc) and allowed to grow to 60-80% confluence. For all experiments, solutions of COP-1 were prepared in DMSO (500 µM) and diluted in DPBS (+Ca, +Mg) to 1.0 µM. CORM-3 solutions were prepared in Millipore water to 5 mM and then diluted in DPBS immediately prior to application to the cells. The DMEM media was removed from the chambers containing cells and the well was washed with DPBS. The buffer was then replaced with buffer that was 50 µM in CORM-3 or a vehicle control and incubated at 37° C. for 15 minutes at which point 100 µL of the buffer was removed from the well, mixed with COP-1 and returned to the cell culture to bring the concentration of probe to 1.0 µM. The cells were then incubated at 37° C. for 30 min prior to imaging. For nuclear staining studies, cells were incubated with 1 µM Hoechst 33342 at 37° C. for 45 min prior to imaging.

Confocal Fluorescence Imaging Experiments

Confocal fluorescence imaging studies were performed with a Zeiss laser scanning microscope 710 with a 40× water objective lens, with Zen 2009 software (Carl Zeiss). COP-1 was excited using a 488 nm Ar laser, and emission collected using a META detector between 500 and 650 nm. Hoechst 33342 was excited with a 405 nm diode laser, and emission collected using a META detector between 450 and 500 nm. The cells were imaged at 37° C. and 5% $CO_2$ throughout the course of the experiment. Image analysis was performed using ImageJ (National Institute of Health).

HEK293T cells were maintained in exponential growth as a monolayer in Dulbecco's Modified Eagle Mediaum (DMEM, Invitrogen) supplemented with 10% fetal bovine serum (FBS, Hyclone), and incubated at 37° C. in 5% $CO_2$. One or two days before imaging, the cells were passaged and plated in phenol red-free medium in a poly-Lysine coated 96-well plate (Corning polylysine coated clear bottomed 96-well plate) and allowed to grow to ~80% confluence. Solutions of COP-1 in DPBS (+Ca, +Mg) buffer were prepared from a 500 µM stock solution in DMSO. The DMEM was removed and cells were covered in DPBS buffer containing COP-1 at various concentrations (0.5-10 µM) or a vehicle control. The cells were incubated for 15 min at 37° C. and then 10 µL of 1 mM CORM-3 was added to half of the wells to bring the concentration to 100 µM. The cells were then incubated for 30 min at 37° C. at which point 10 µL of the WST reagent solution (Roche) was added to all wells. The cells were incubated at 37° C. and absorbance readings were taken at 55, 75, and 100 min using a Spectramax M2 plate reader.

Results and Discussion

The overall strategy for imaging CO in live biological systems relies on exploiting selective CO-induced reaction chemistry for its detection. Recent work from our laboratory on reaction-based fluorescent probes for imaging $H_2O_2$ (Lippert, A. R.; Van, d. B. G. C.; Chang, C. J. *Acc. Chem. Res.* 2011, 44, 793-804; Chang, M. C. Y.; Pralle, A.; Isacoff, E. Y.; Chang, C. J. *J. Am. Chem. Soc.* 2004, 126, 15392-15393; Miller, E. W.; Albers, A. E.; Pralle, A.; Isacoff, E. Y.; Chang, C. J. *J. Am. Chem. Soc.* 2005, 127, 16652-16659; Miller, E. W.; Tulyanthan, O.; Isacoff, E. Y.; Chang, C. J. *Nat. Chem. Biol.* 2007, 3, 263-267; Srikun, D.; Miller, E. W.; Domaille, D. W.; Chang, C. J. *J. Am. Chem. Soc.* 2008, 130, 4596-4597; Dickinson, B. C.; Chang, C. J. *J. Am. Chem. Soc.* 2008, 130, 9638-9639; Miller, E. W.; Dickinson, B. C.; Chang, C. J. *Proc. Natl. Acad. Sci. U.S.A.* 2010, 107, 15681-15686; Srikun, D.; Albers, A. E.; Nam, C. I.; Iavarone, A. T.; Chang, C. J. *J. Am. Chem. Soc.* 2010, 132, 4455-4465; and Dickinson, B. C.; Peltier, J.; Stone, D.; Schaffer, D. V.; Chang, C. J. *Nat. Chem. Biol.* 2011, 7, 106-112) and $H_2S$ (Lippert, A. R.; New, E. J.; Chang, C. J. *J. Am. Chem. Soc.* 2011, 133, 10078-10080) have taken advantage of the respective nucleophilic oxidative and reductive abilities of these small molecules. In contrast, CO is not a particularly nucleophilic or electrophilic species and is better known for its inorganic coordination chemistry and subsequent organometallic reactivity. As such, we envisioned metal-mediated carbonylation chemistry as a potential means to design a reaction-based fluorescent CO probe as covalent incorporation of CO into a dye scaffold can significantly alter its electronic characteristics. In particular, we turned our attention to palladium owing to the established reactivity of this metal in catalytic carbonylation reactions (Dupont, J.; Consorti, C. S.; Spencer, J. *Chem. Rev.* 2005, 105, 2527-2571; Aguilar, D.; Cuesta, L.; Nieto, S.; Serrano, E.; Urriolabeitia, E. P. *Curr. Org. Chem.* 2011, 15, 3441-3464; Fuchita, Y.; Tsuchiya, H.; Miyafuji, A. *Inorg. Chim. Acta* 1995, 233, 91-96; Barr, N.; Bartley, J. P.; Clark, P. W.; Dunstan, P.; Dyke, S. F. *J. Organomet. Chem.* 1986, 302, 117-126; Dupont, J.; Pfeffer, M.; Daran, J. C.; Jeannin, Y. *Organometallics* 1987, 6, 899-901; Ryabov, A. D. *Synthesis* 1985, 233-252; and Li, H.; Cai, G.-X.; Shi, Z.-J. *Dalton Trans.* 2010, 39, 10442-10446), as well as recent reports demonstrating the compatibility of organometallic reactions with cellular systems, including Ahn's indicators for palladium/platinum (Santra, M.; Ko, S.-K.; Shin, I.; Ahn, K. H. *Chem. Commun.* 2010, 46, 3964-3966) and Meggers' ruthenium-induced allyl carbamate cleavage (Streu, C.; Meggers, E. *Angew. Chem. Int. Ed.* 2006, 45, 5645-5648), where cell viability was maintained. Additionally, Bradley and co-workers elegantly illustrated the use of palladium-functionalized microspheres to elicit both deallylation and cross-coupling reactions in live cells (Yusop, R. M.; Unciti-Broceta, A.; Johansson, E. M. V.; Sanchez-Martin, R. M.; Bradley, M. *Nat. Chem.* 2011, 3, 239-243). Based on these considerations, we designed and synthesized the cyclopalladated species COP-1, anticipating that the presence of palladium would quench the fluorescence of the BODIPY core via heavy atom electronic effects and that upon binding CO, a carbonylation reaction would concomitantly release reduced Pd(0) and a more fluorescent species. To this end, we prepared COP-1 by alkylation of the benzyl chloride 2 with dimethylamine and subsequent cyclometallation with $Pd(OAc)_2$, which was then converted to the chloride dimer (Scheme 1).

Figure 2A:
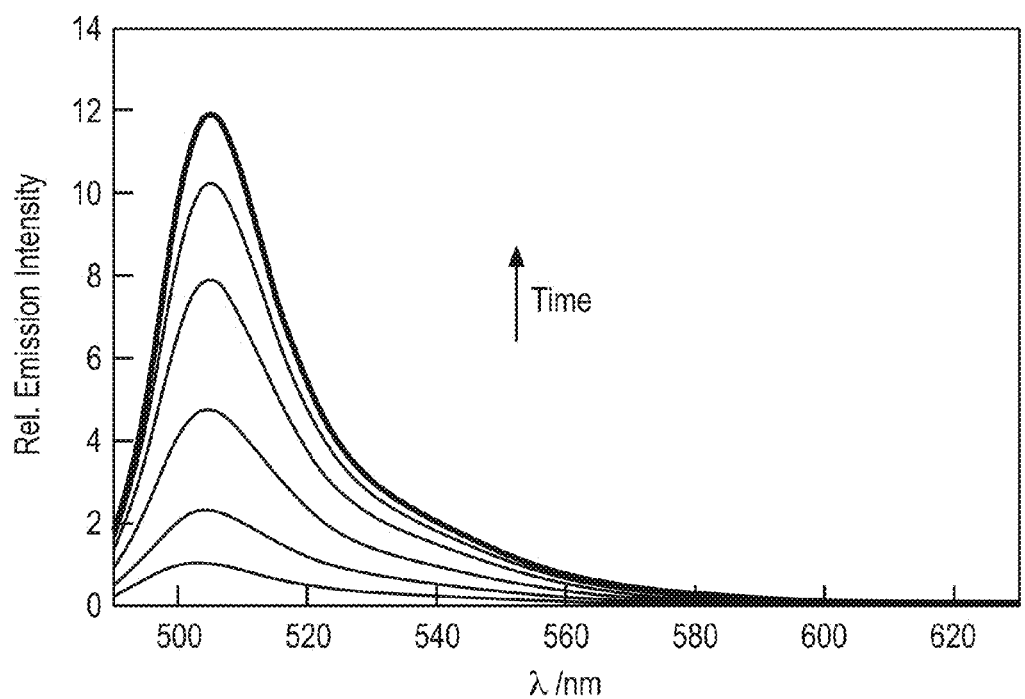
FIGS. 2A and 2B show COP-1 show a robust and selective turn-on response to CO in buffered aqueous solution.
Figure 4:
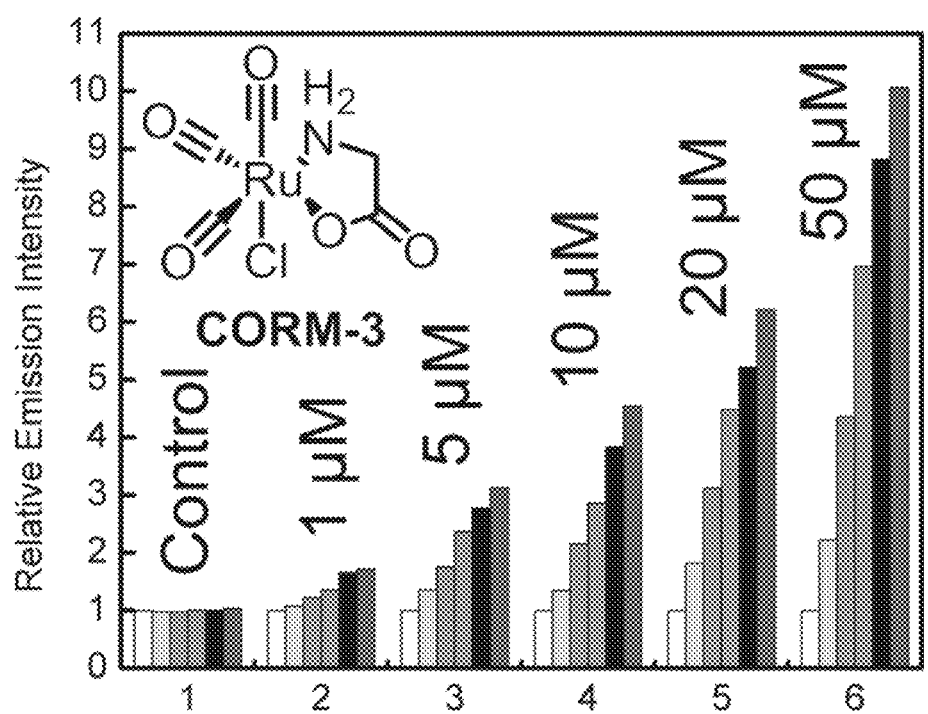
FIG. 4 shows a dose dependent increase in integrated fluorescence intensity over time. The concentration of CORM is indicated above each set of experiments and the bars represent the normalized integrated fluorescence intensity at various timepoints up to one hour.
Figure 5:
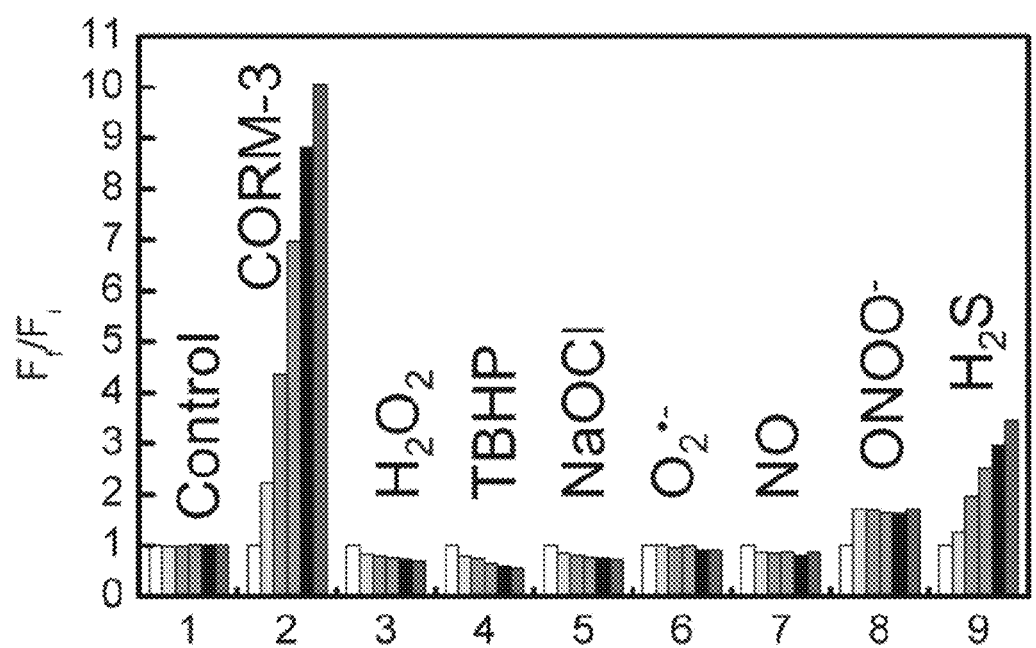
FIG. 5 shows the selectivity of COP-1 for CO as compared to the other indicated reactive oxygen, nitrogen and sulfur species. The specific species is indicated above each set of experimental data and the bars represent increasing timepoints up to one hour (red bar).
Figure 6:
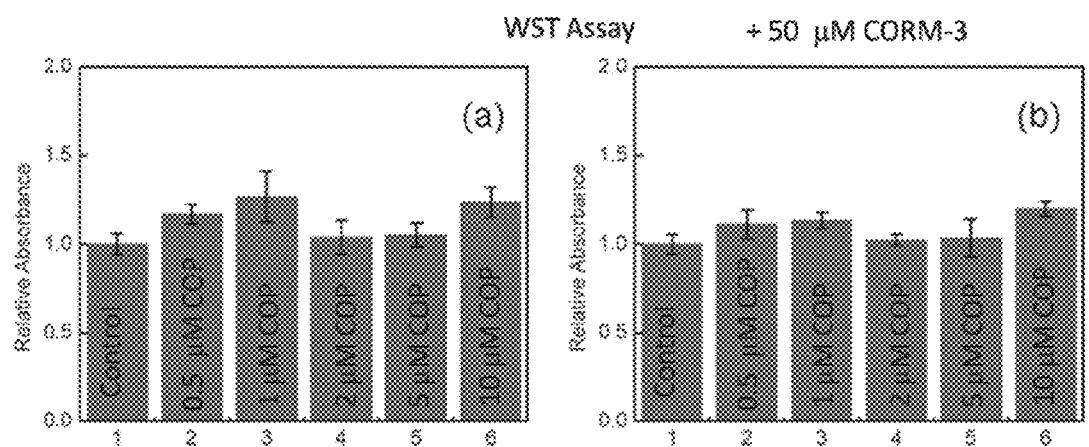
FIGS. 6A and 6B show the WST assay results for HEK293T cells. Each bar represents a normalized average of at least three and up to six wells of a 96-well plate. WST assay performed in 96 well plate for the evaluation of cell viability after the cells have been treated with (a) COP-1 at various concentrations as indicated and (b) COP-1 at various concentrations as indicated and CORM-3 (50 µM).
Figure 7:
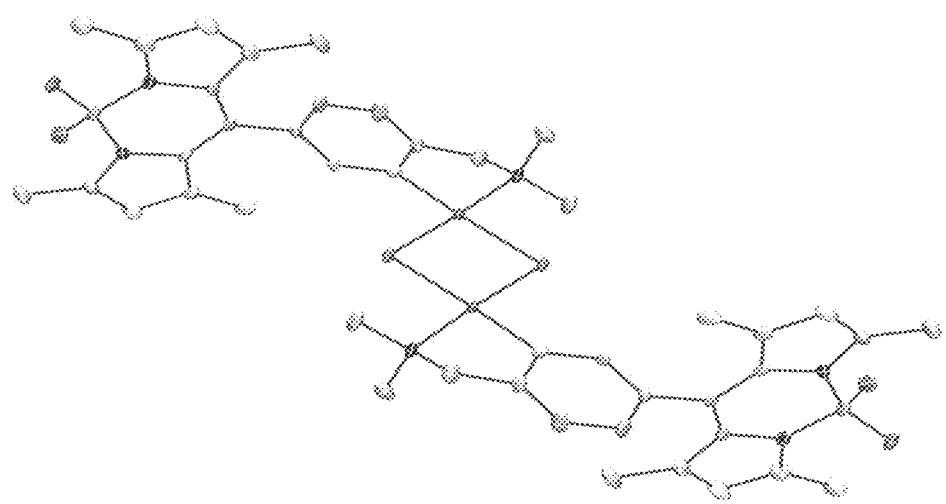
FIG. 7 shows a crystal structure of COP-1 dimer.

With COP-1 in hand, we tested its fluorescence properties and CO reactivity in aqueous solution buffered to physiological pH. For the present in vitro analysis, we utilized the water soluble complex CORM-3 [$Ru(CO)_3Cl(glycinate)$] as an easy-to-handle CO source (Clark, J. E.; Naughton, P.; Shurey, S.; Green, C. J.; Johnson, T. R.; Mann, B. E.; Foresti, R.; Motterlini, R. *Circ. Res.* 2003, 93, e2-e8; and Motterlini, R.; Mann, B. E.; Johnson, T. R.; Clark, J. E.; Foresti, R.; Green, C. J. *Curr. Pharm. Des.* 2003, 9, 2525-2539). As expected, COP-1 is weakly fluorescent in DPBS buffered to pH 7.4 ($\mu_{em}$=503 nm, Φ=0.01; see FIG. 9). Addition of 50 µM CORM-3 to a solution of COP-1 at 37° C. triggers a robust fluorescence turn-on response owing to CO-induced formation of the carbonylation product 4, which was synthesized and characterized independently for verification ($\lambda_{max}$=499 nm, ε=23 000 $M^{-1}$ $cm^{-1}$, $\lambda_{em}$=507 nm, Φ=0.44; see FIG. 8). Interestingly, this acid is the major product in aqueous solution, in contrast to the dealkylative amide product typically observed in organic solutions (Dupont, J.; Pfeffer, M.; Daran, J. C.; Jeannin, Y. *Organometallics* 1987, 6, 899-901). Within 60 min of reaction under these conditions, COP-1 produced a 10-fold increase in fluorescence (FIG. 2A). Moreover, we observe a dose-dependent response for COP-1 to CORM-3 down to 1 μM (~28 ppb CO) levels (FIG. 4).

Figure 2B:
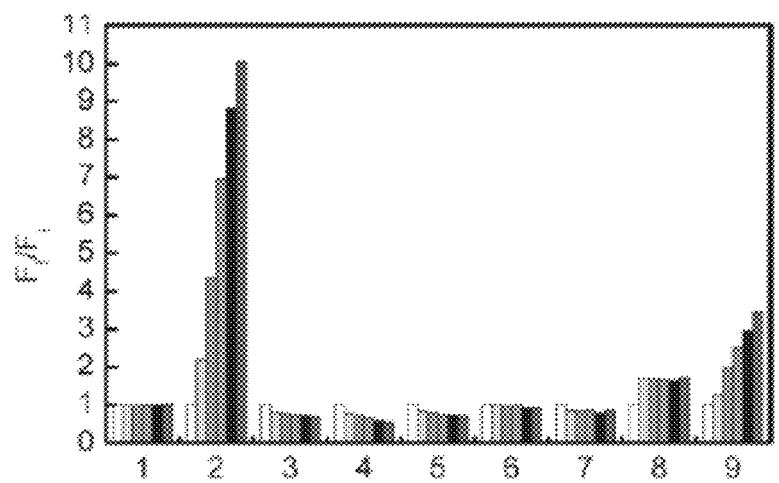

Moreover, the fluorescence turn-on response for COP-1 was found to have good selectivity over other biologically relevant reactive oxygen, nitrogen, and sulfur species, including $H_2O_2$, tert-butyl hydroperoxide (tBuOOH), hypochlorite ($OCl^-$), superoxide ($O_2^-$), NO, peroxynitrite (ONOO—), and $H_2S$, as exposure of COP-1 to these molecules did not trigger fluorescence responses to the same extent as exposure to CO (FIG. 2B).

Figure 3:
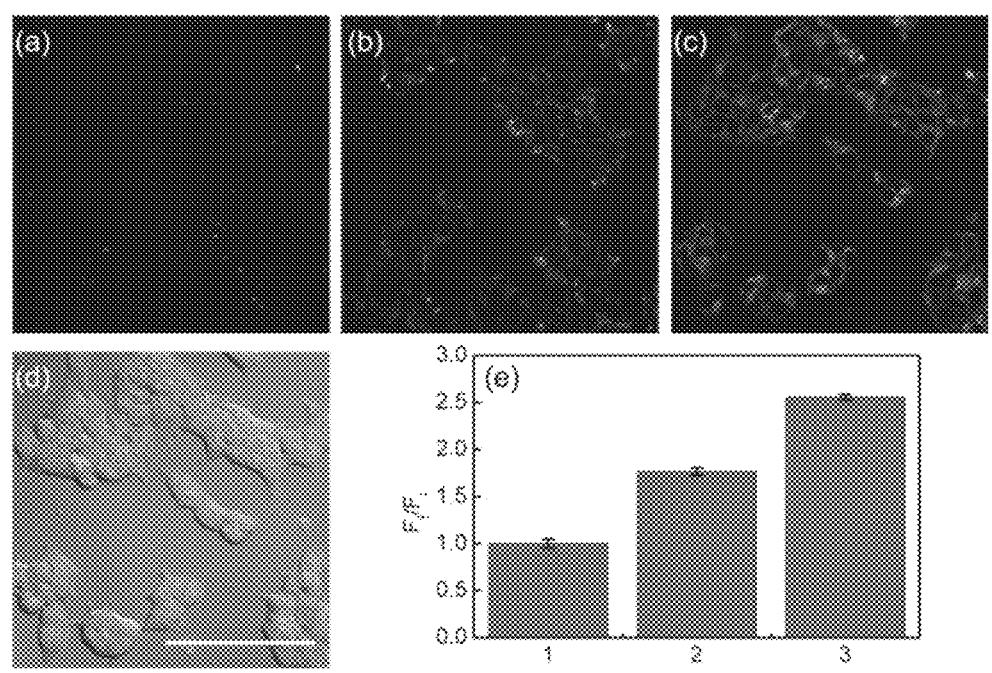
FIGS. 3A-3E show confocal microscopy images of CO detection in live HEK293T cells using COP-1 and an WST assay performed in 96 well plate for the evaluation of cell viability after the cells have been treated with (a) COP-1 at various concentrations as indicated and (b) COP-1 at various concentrations as indicated and CORM-3 (50 µM).
Figure 9:
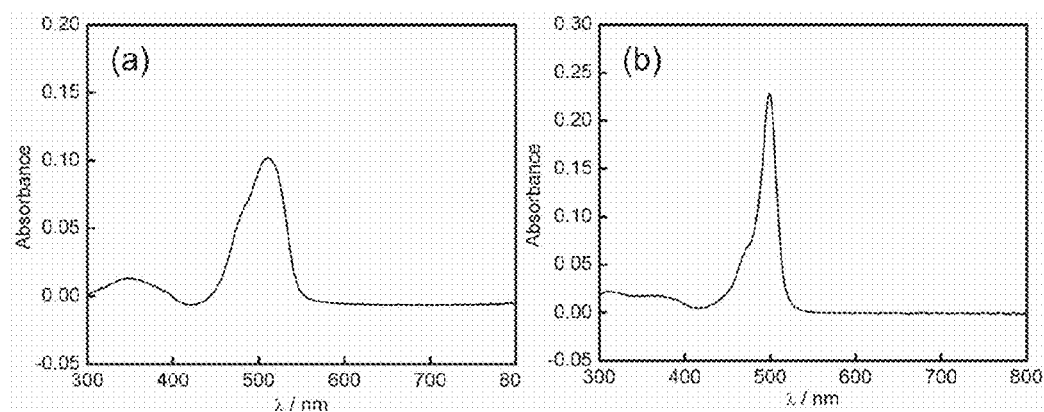
FIGS. 9A and 9B show an absorbance spectra of (a) 4 µM COP-1 (b) 10 µM 4.
Figure 10A:
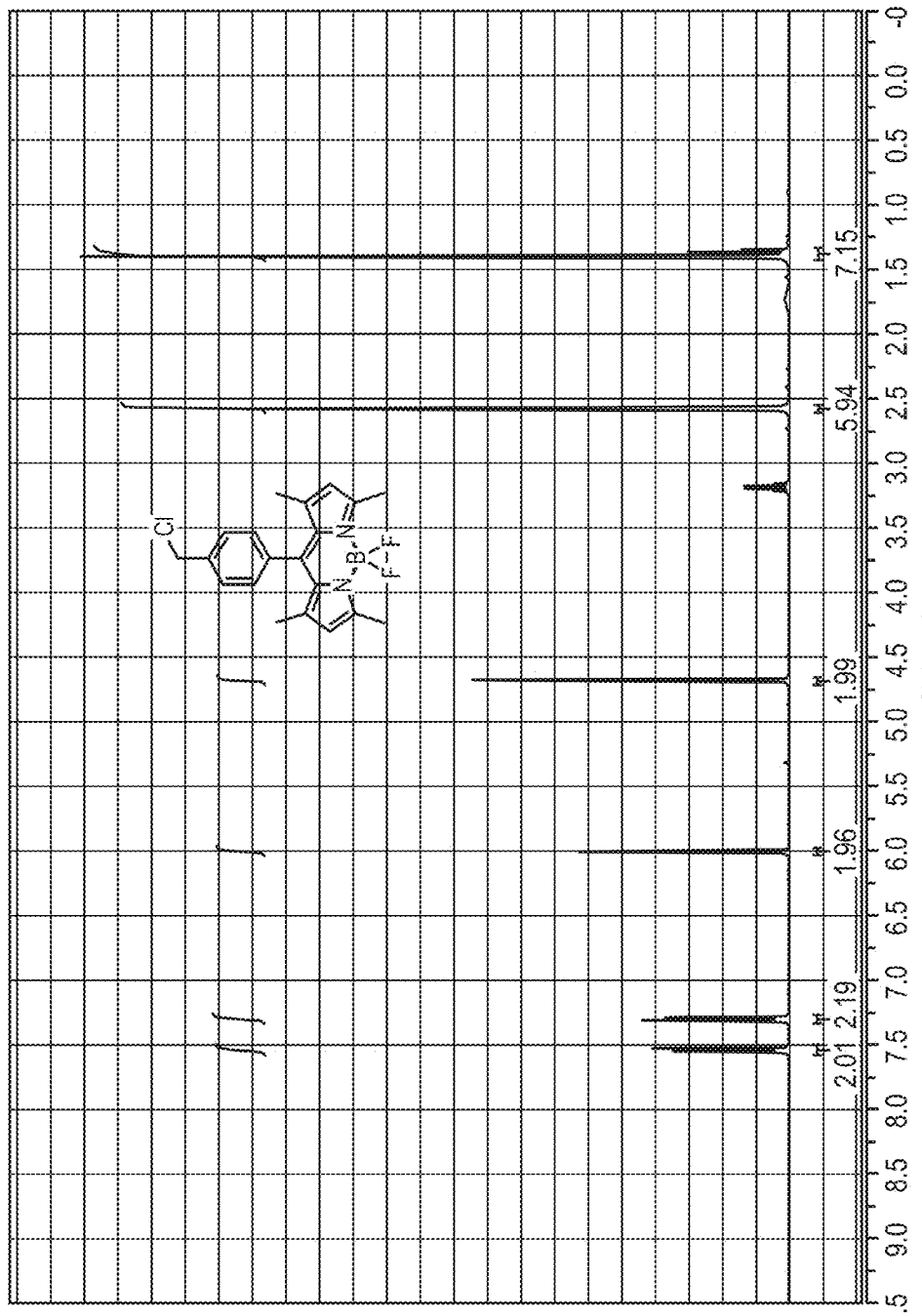
FIGS. 10A and 10B show $^1H$ and $^{13}C$ NMR spectra of compound 2.
Figure 10B:
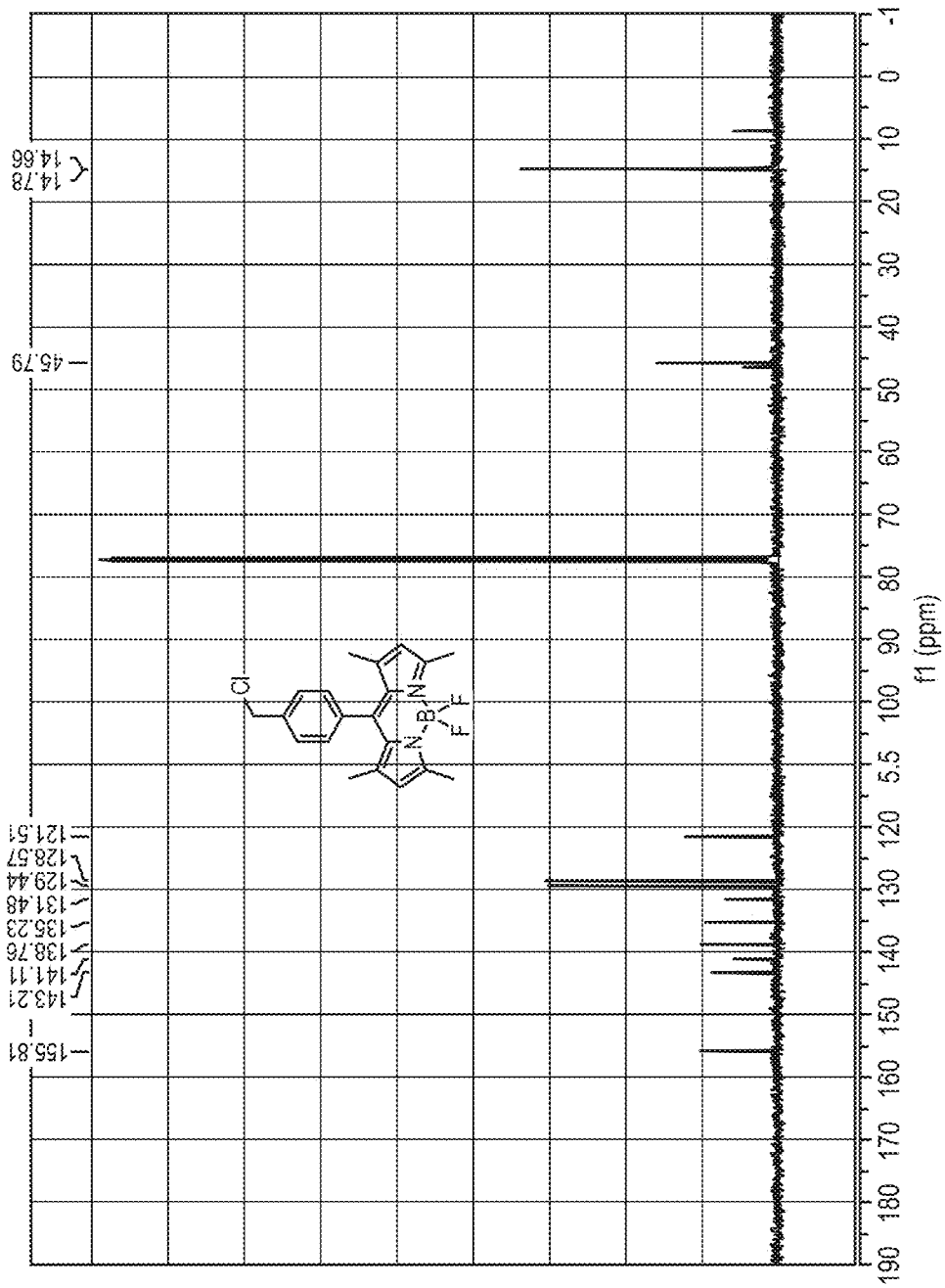
Figure 11A:
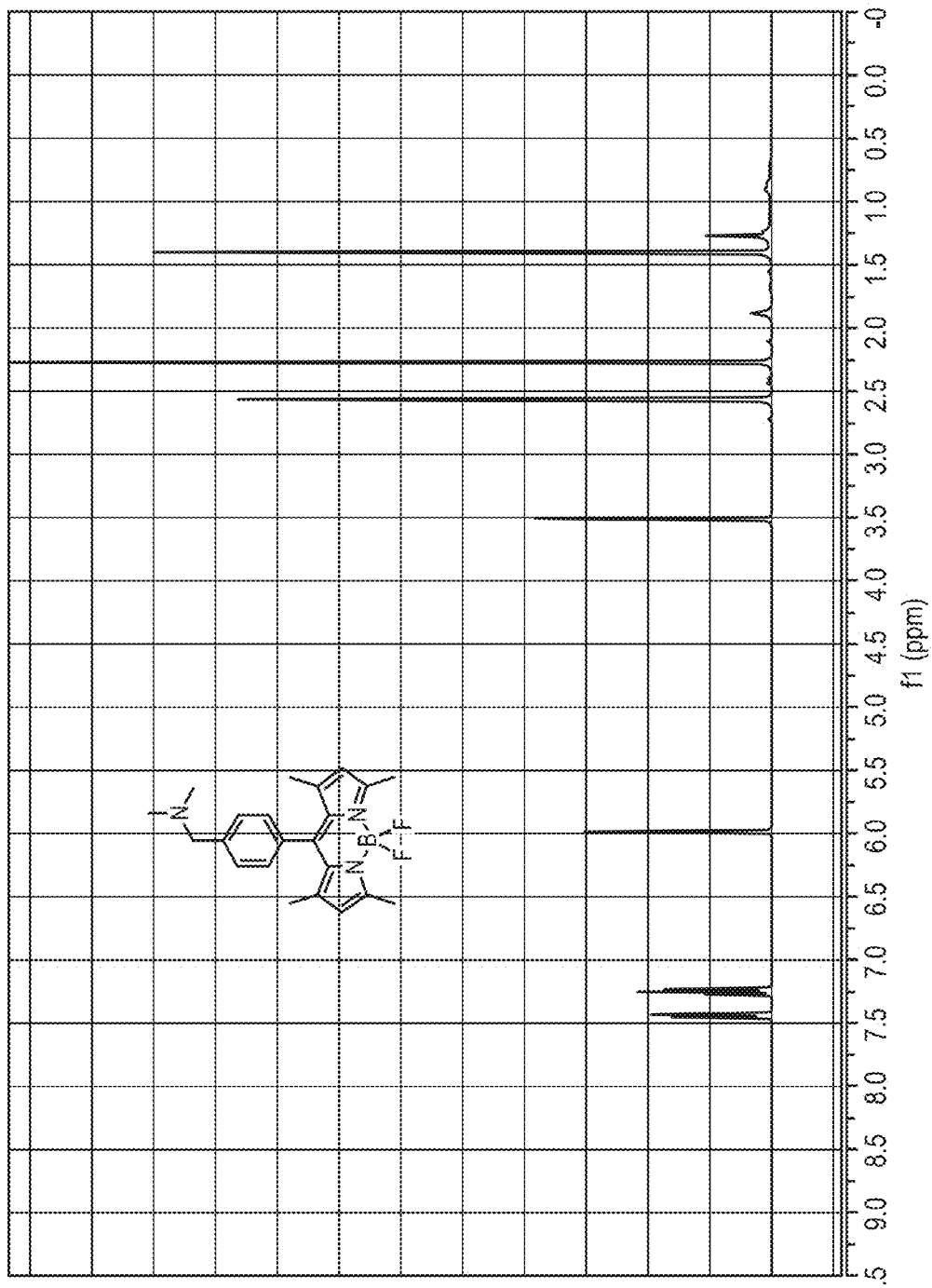
FIGS. 11A and 11B show $^1H$ and $^{13}C$ NMR spectra of compound 3.
Figure 11B:
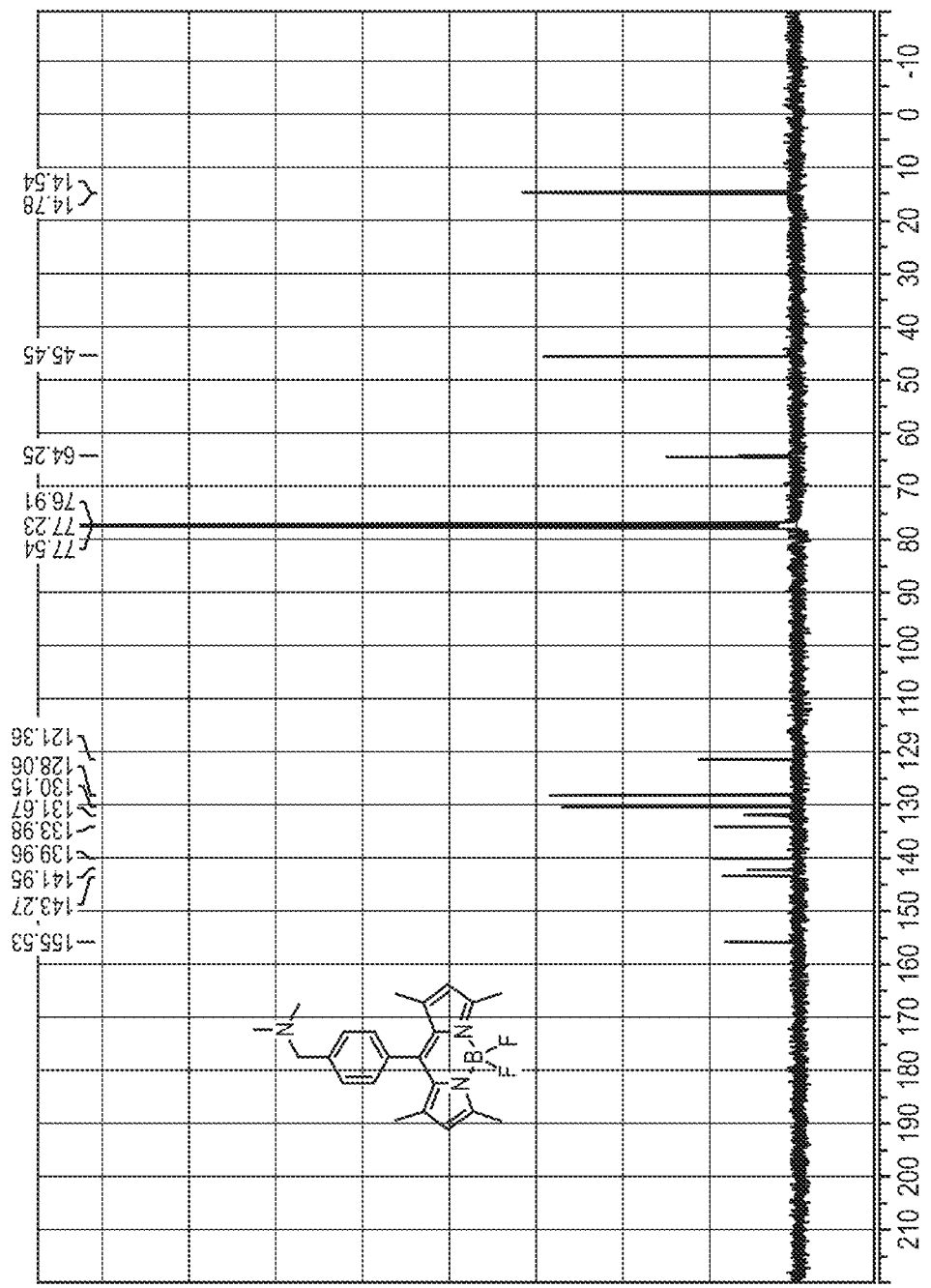
Figure 12A:
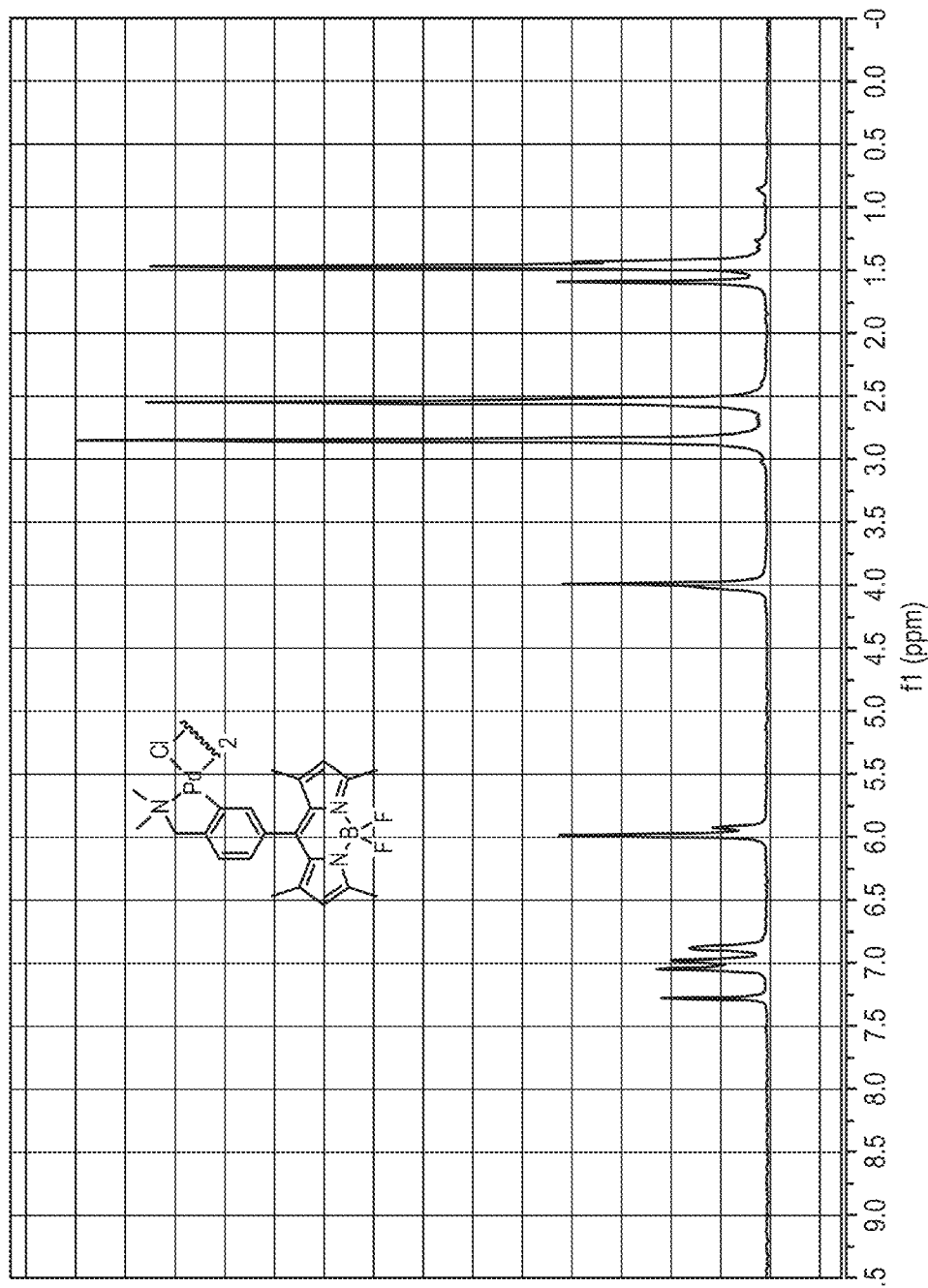
FIGS. 12A and 12B show $^1H$ and $^{13}C$ NMR spectra of COP-1.
Figure 12B:
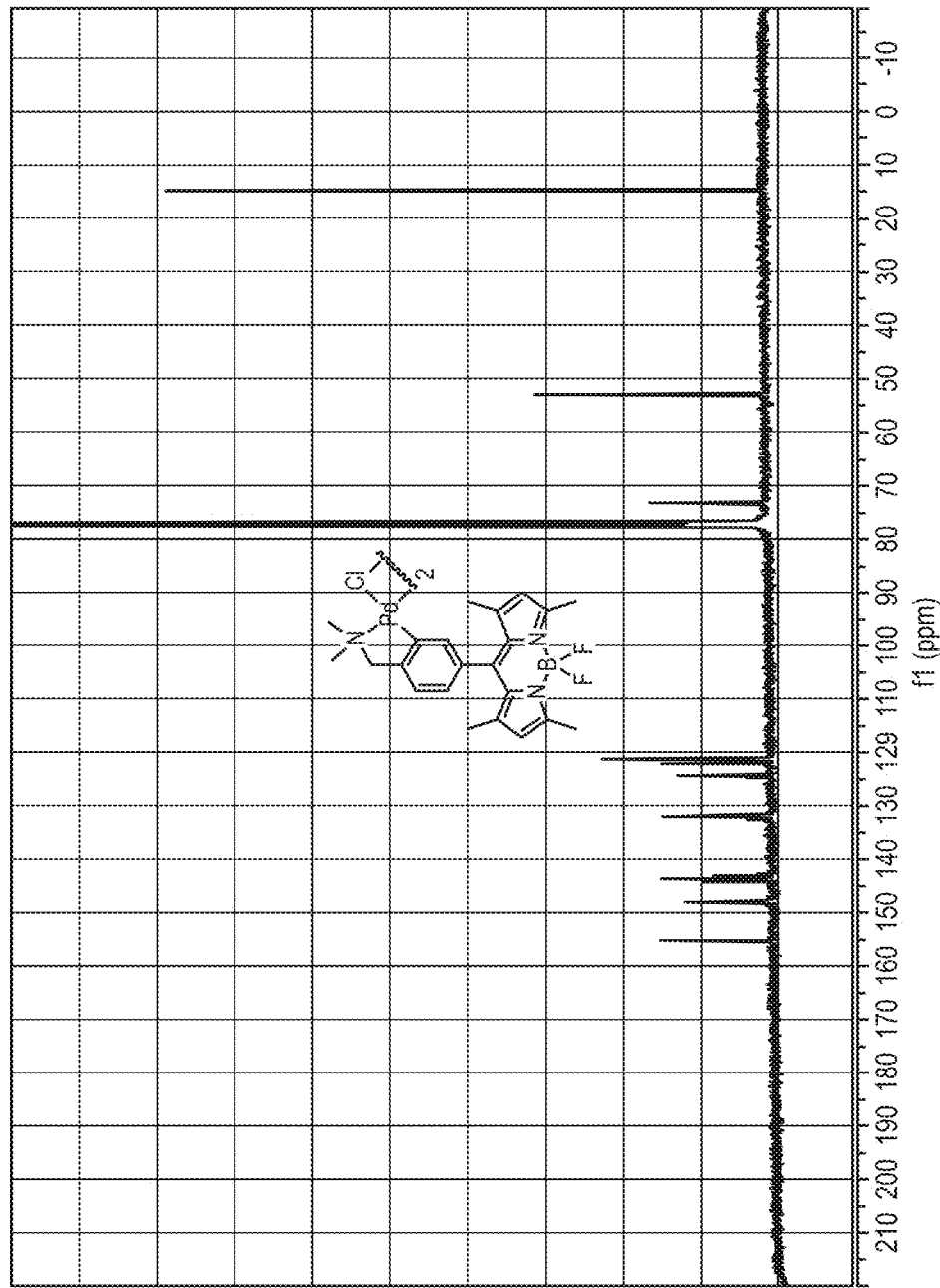
Figure 13A:
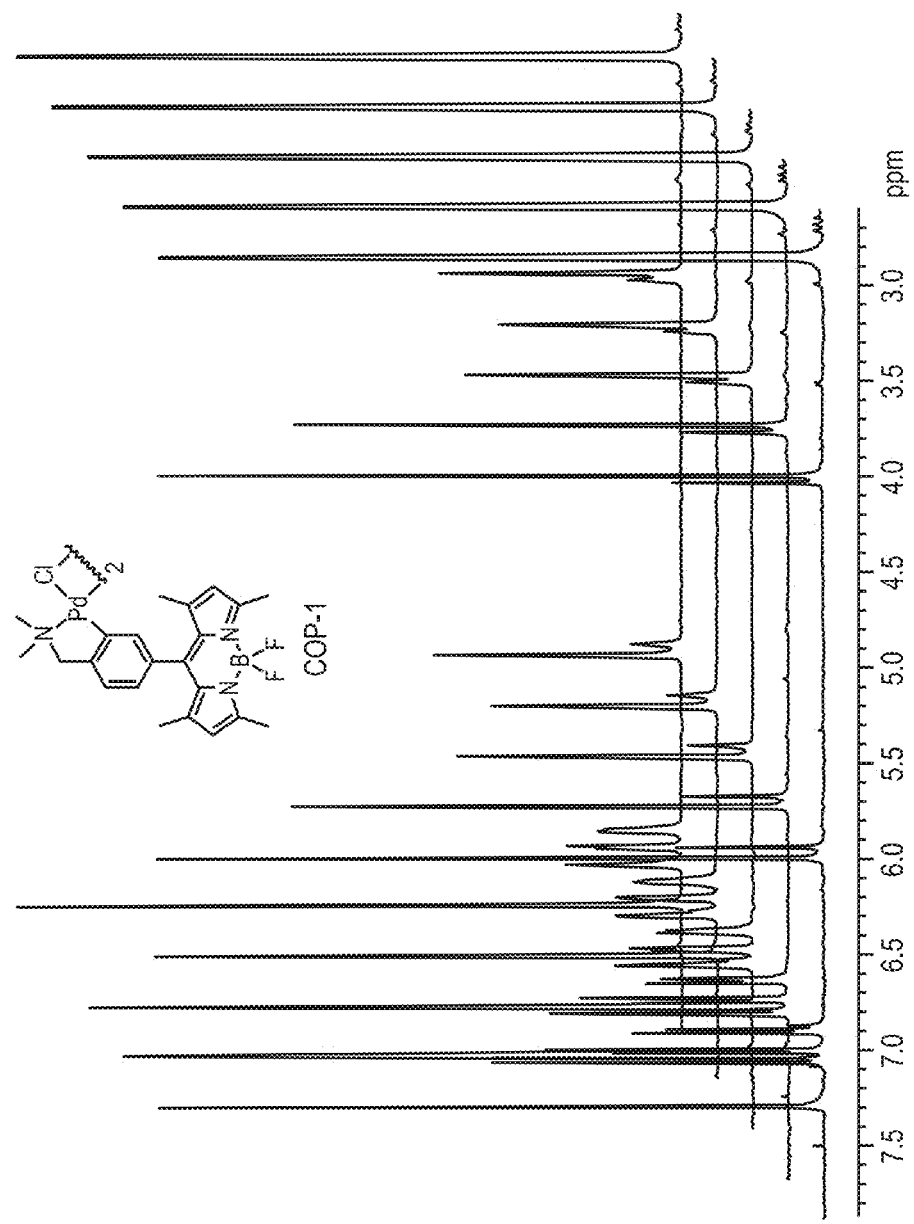
FIGS. 13A and 13B show $^1H$ NMR spectra of COP-1 at 20° C., 30° C., 40° C., 48° C., 51.5° C.
Figure 13B:
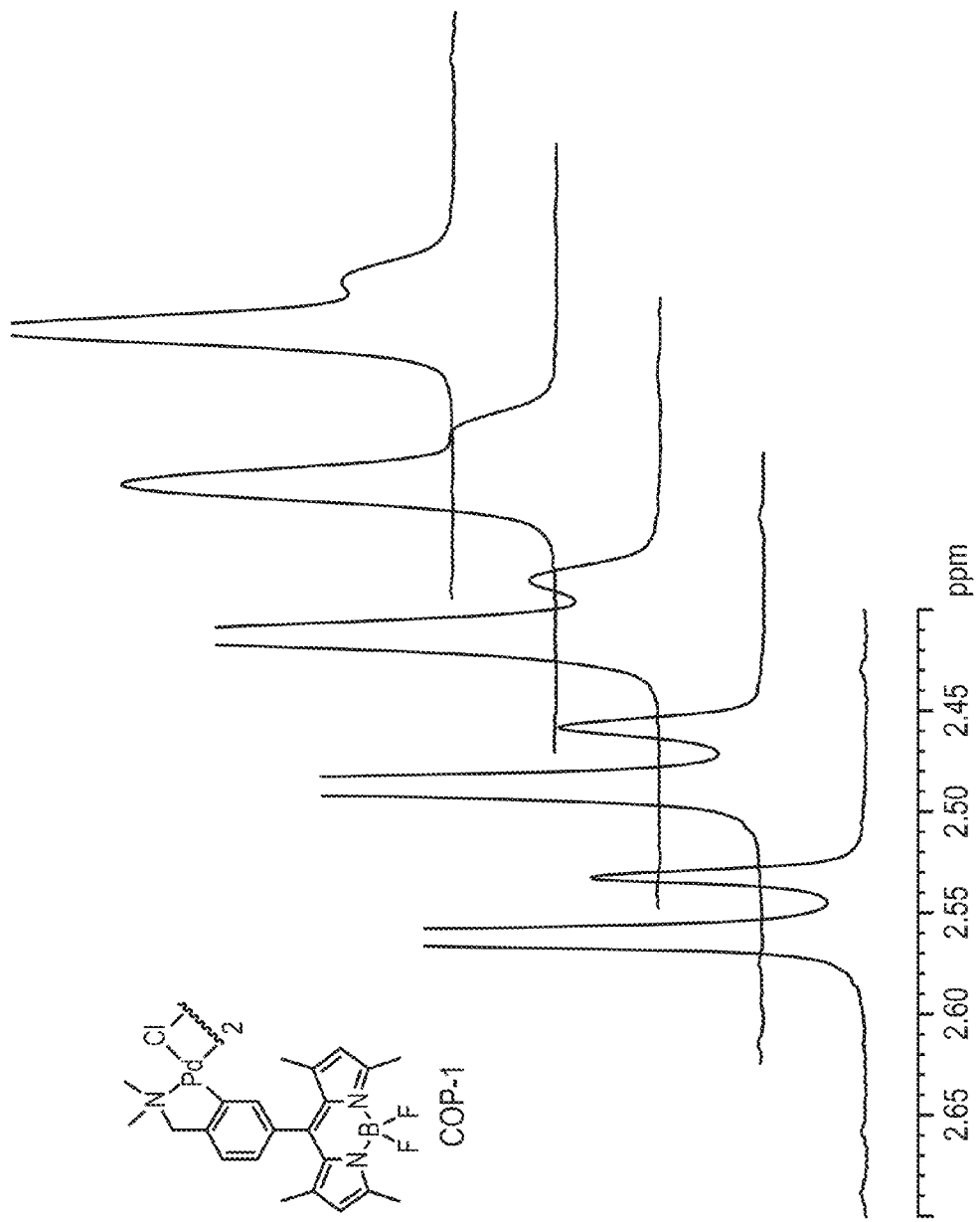
Figure 14A:
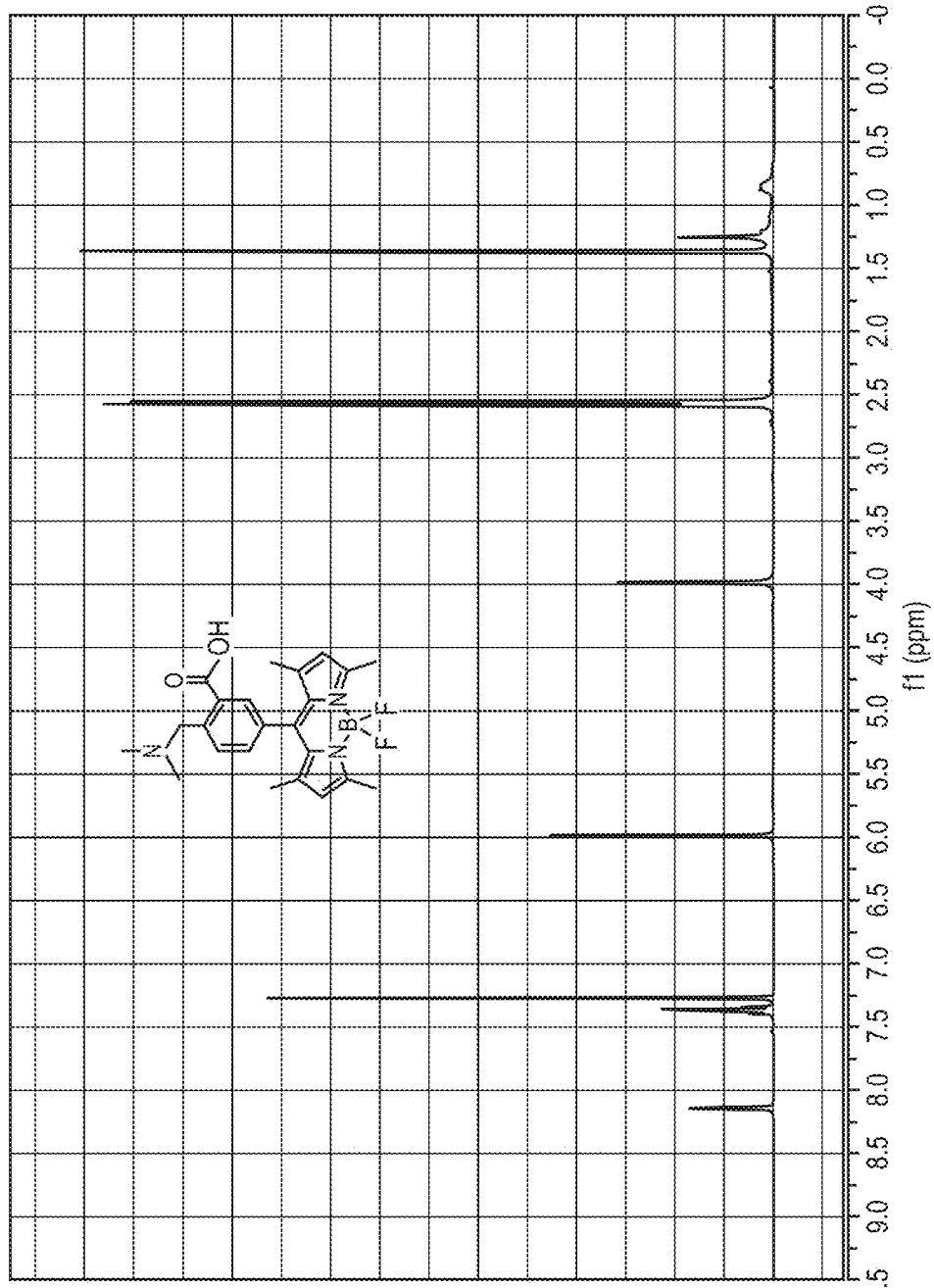
FIGS. 14A and 14B show $^1H$ and $^{13}C$ NMR spectra of compound 4.
Figure 14B:
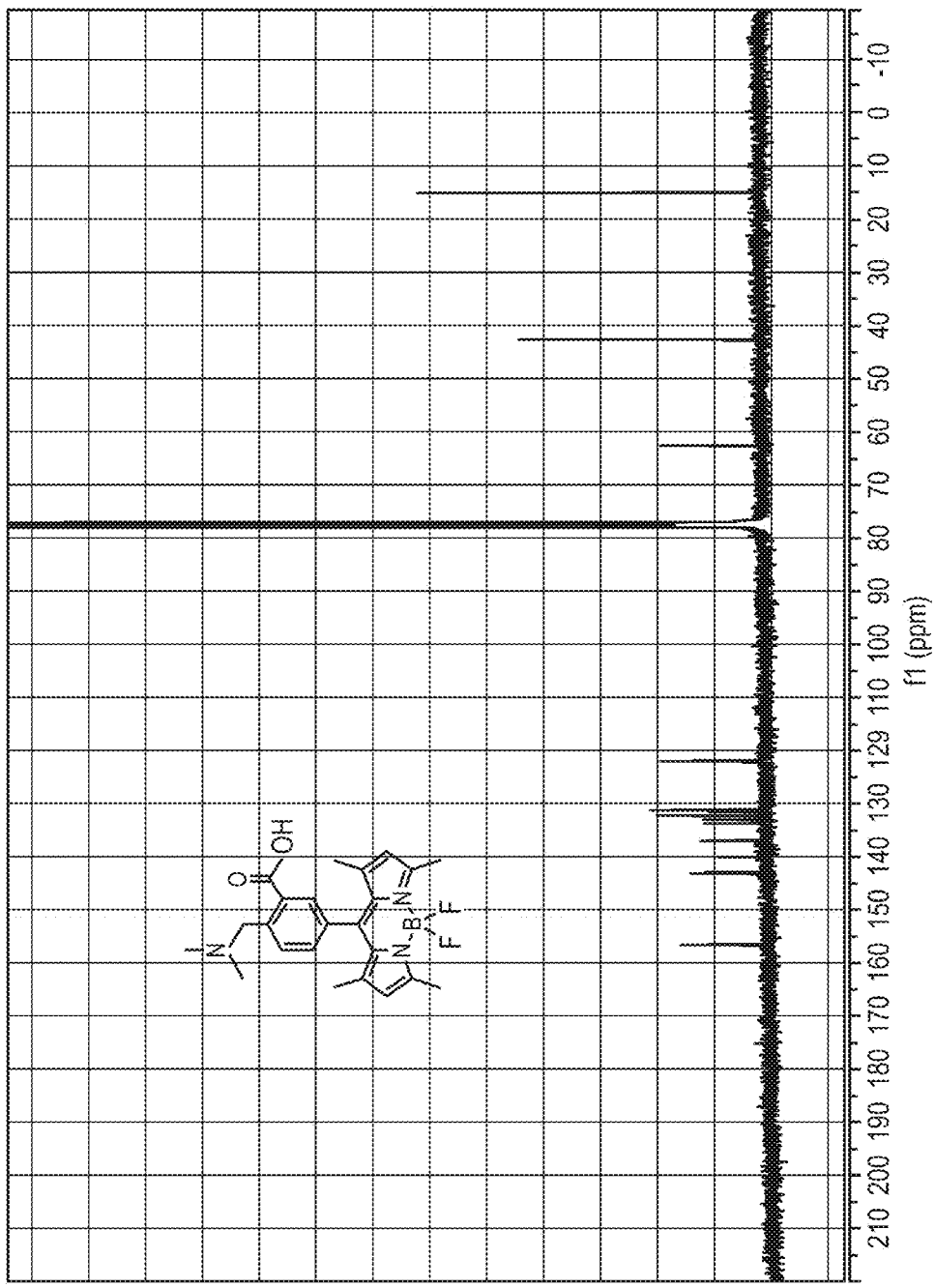
Figure 15:
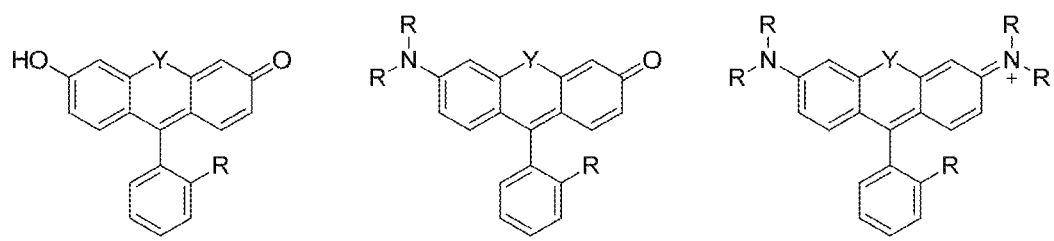
FIG. 15. Exemplary compounds of the invention. Exemplary moieties for R include "aryl group substituents" as this groups is defined herein.

Finally, we evaluated the ability of COP-1 to visualize changes in CO levels in live cells using confocal microscopy. HEK293T cells were either incubated with CORM-3 (5 μM or 50 μM) or a vehicle control and then the cells were treated with 1 μM COP-1 (FIG. 2). A significant and dose-dependent increase in intracellular fluorescence was observed in CORM-3 treated cells (FIGS. 3B, 3C and 3E) over vehicle control samples (FIG. 3A and FIG. 3E). In addition, we performed two independent types of assays to show that the palladium-based probe and its reactivity was nontoxic to the cellular specimens and compatible with live-cell imaging over the course of these experiments. First, we acquired brightfield images that were overlaid with fluorescent images of the cells stained with Hoescht 33342 nuclear stain that clearly show intact and viable nuclei (FIG. 3D). Second, to further validate cell viability, a WST cell proliferation assay was performed over a range of probe concentrations (500 nM to 10 mM), with and without the addition of CORM-3 (100 μM). Cell viability remained constant over the range of probe concentrations evaluated (FIG. 9). We note that the concentrations of CORM-3 employed are well within the therapeutic window, as up to 500 μM CORM-3 has been shown to not alter cell viability and the added CORM-3 in these experiments is 1-2 orders of magnitude less than this upper limit (Vadori, M.; Seveso, M.; Besenzon, F.; Bosio, E.; Tognato, E.; Fante, F.; Boldrin, M.; Gavasso, S.; Ravarotto, L.; Mann, B. E.; Simioni, P.; Ancona, E.; Motterlini, R.; Cozzi, E. *Xenotransplantation* 2009, 16, 99-114; and Desmard, M.; Davidge, K. S.; Bouvet, O.; Morin, D.; Roux, D.; Foresti, R.; Ricard, J. D.; Denamur, E.; Poole, R. K.; Montravers, P.; Motterlini, R.; Boczkowski, J. *FASEB J.* 2009, 23, 1023-1031). Alternatively, the endogenous CO concentrations produced by heme oxygenase are less well understood due to poor correlation between carboxyhemoglobin levels and experiment outcomes (Foresti, R.; Bani-Hani, M. G.; Motterlini, R. *Intensive Car Med.* 2008, 34, 649-658). Regardless, endogenous CO levels are estimated be much lower and vary over large ranges depending on cell type.

The present invention has been illustrated by reference to various exemplary embodiments and examples. As will be apparent to those of skill in the art other embodiments and variations of this invention may be devised by others skilled in the art without departing from the true spirit and scope of the invention. The appended claims are to be construed to include all such embodiments and equivalent variations.

The disclosures of each and every patent, patent application, and publication cited herein are hereby incorporated herein by reference in their entirety.

What is claimed is:

1. A fluorogenic compound, which is a probe for CO, and which detectably fluoresces upon carbonylation with CO, said probe having a structure according to Formula I:

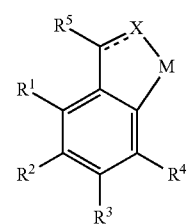

wherein,

M is a metal capable of catalyzing carbonylation by CO of the ring system to which it is bound, said metal optionally bound to one, two or more additional ligands;

the dashed line (- - - -) indicates a degree of unsaturation that is either present or absent;

X is a moiety selected from the group consisting of $NR^6R^7$, $NR^6$, $PR^6R^7$ and $SR^6$ wherein, $R^6$ and $R^7$ are members independently selected from the group consisting of H, substituted or unsubstituted alkyl, substituted or unsubstituted heteroalkyl, substituted or unsubstituted aryl, and substituted or unsubstituted heteroaryl, and $R^6$ and $R^7$, together with the atoms to which they are bound are optionally joined to form a 5- to 7-membered ring system which is a member selected from the group consisting of substituted or unsubstituted cycloalkyl, substituted or unsubstituted heterocycloalkyl, substituted or unsubstituted aryl and substituted or unsubstituted heteroaryl;

$R^1$, $R^2$, $R^3$, $R^4$, and $R^5$ are members independently selected from the group consisting of H, substituted or unsubstituted alkyl, substituted or unsubstituted heteroalkyl, substituted or unsubstituted aryl, substituted or unsubstituted heteroaryl, halogen, CN, $CF_3$, acyl, $—SO_2NR^{12}R^{13}$, $—NR^{12}R^{13}$, $—OR^{12}$, $—S(O)_2R^{12}$, $—C(O)R^{12}$, $—COOR^{12}$, $—CONR^{12}R^{13}$, $—S(O)_2OR^{12}$, $—OC(O)R^{12}$, $—C(O)NR^{12}R^{13}$, $—NR^{12}C(O)R^{13}$, $—NR^{12}SO_2R^{13}$, $NR^{12}C(O)NR^{13}R^{14}$, $C(NR^{12})R^{13}$, and $—NO_2$, and at least one of $R^1$, $R^2$, $R^3$, and $R^4$ is a fluorophore, wherein said fluorophore is maintained in a quenched state by interacting with M, wherein, $R^{12}$, $R^{13}$ and $R^{14}$ are members independently selected from the group consisting of H, substituted or unsubstituted alkyl, substituted or unsubstituted heteroalkyl, substituted or unsubstituted aryl, and substituted or unsubstituted heteroaryl, and two or more of $R^{12}$, $R^{13}$, and $R^{14}$, together with the atoms to which they are bound, are optionally joined to form a 5- to 7-membered ring system which is a member selected from the group consisting of substituted or unsubstituted cycloalkyl, substituted or unsubstituted heterocycloalkyl, substituted or unsubstituted aryl and substituted or unsubstituted heteroaryl, and two or more of $R^1$, $R^2$, $R^3$, $R^4$, and are optionally joined to form a 5-7-membered ring system selected from the group consisting of substituted or unsubstituted cycloalkyl, substituted or unsubstituted heterocycloalkyl, substituted or unsubstituted aryl and substituted or unsubstituted heteroaryl with the proviso that if two or more of $R^1$, $R^2$, $R^3$, R⁴, and R5 are joined to form said ring system, then none of said two or more of R¹, R², R³, R⁴, and R⁵ so joined are said fluorophore;
wherein said fluorophore has the formula:

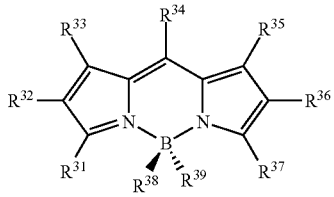

wherein R³¹, R³², R³³, R³⁴, R³⁵, R³⁶ and R³⁷ are members independently selected from the group consisting of H, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein at least one of R³¹, R³², R³³, R³⁴, R³⁵, R³⁶ and R³⁷ comprises a bond to the remainder of the compound according to Formula I; and R³⁸ and R³⁹ are members independently selected from the group consisting of H, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, and NR⁴⁰R⁴¹ wherein R⁴⁰ and R⁴¹ are members independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

2. A fluorogenic compound, which is a probe for CO, and which detectably fluoresces upon carbonylation with CO, said probe having a structure according to Formula II:

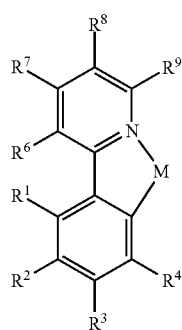

wherein,
M is a metal capable of catalyzing carbonylation by CO of the ring system to which it is bound, said metal optionally bound to one, two or more additional ligands;
R¹, R², R³, and R⁴ are members independently selected from the group consisting of H, substituted or unsubstituted alkyl, substituted or unsubstituted heteroalkyl, substituted or unsubstituted aryl, substituted or unsubstituted heteroaryl, halogen, CN, CF₃, acyl, —SO₂NR¹²R¹³, —NR¹²R¹³, —OR¹², —S(O)₂R¹², —C(O)R¹², —COOR¹², —CONR¹²R¹³, —S(O)₂OR¹², —OC(O)R¹², —C(O)NR¹²R¹³, —NR¹²C(O)R¹³, —NR¹²SO₂R¹³, NR¹²C(O)NR¹³R¹⁴, C(NR¹²)R¹³, and —NO₂, and at least one of R¹, R², R³, and R⁴ is a fluorophore, wherein said fluorophore is maintained in a quenched state by interacting with M, wherein, R¹², R¹³ and R¹⁴ are members independently selected from the group consisting of H, substituted or unsubstituted alkyl, substituted or unsubstituted heteroalkyl, substituted or unsubstituted aryl, and substituted or unsubstituted heteroaryl, and two or more of R¹², R¹³, and R¹⁴, together with the atoms to which they are bound, are optionally joined to form a 5- to 7-membered ring system which is a member selected from the group consisting of substituted or unsubstituted cycloalkyl, substituted or unsubstituted heterocycloalkyl, substituted or unsubstituted aryl and substituted or unsubstituted heteroaryl, and two or more of R¹, R², R³, and R⁴ are optionally joined to form a 5-7-membered ring system selected from the group consisting of substituted or unsubstituted cycloalkyl, substituted or unsubstituted heterocycloalkyl, substituted or unsubstituted aryl and substituted or unsubstituted heteroaryl with the proviso that if two or more of R¹, R², R³, and R⁴ are joined to form said ring system, then none of said two or more of R¹, R², R³, and R⁴ so joined are said fluorophore;

R⁶, R⁷, R⁸, and R⁹ are members independently selected from the group consisting of H, substituted or unsubstituted alkyl, substituted or unsubstituted heteroalkyl, substituted or unsubstituted aryl, substituted or unsubstituted heteroaryl, halogen, CN, CF₃, acyl, —SO₂NR¹⁵R¹⁶, —NR¹⁵R¹⁶, —OR¹⁵, —S(O)₂R¹⁵, —C(O)R¹⁵, —COOR¹⁵, —CONR¹⁵R¹⁶, —S(O)₂OR¹⁵, —OC(O)R¹⁵, —C(O)NR¹⁵R¹⁶, —NR¹⁵C(O)R¹⁶, —NR¹⁵SO₂R¹⁶, NR¹⁵C(O)NR¹⁶R¹⁷, C(NR¹⁵)R¹⁶, and —NO₂, wherein two or more of R¹⁵, R¹⁶, and R¹⁷, together with the atoms to which they are bound, are joined to form a 5- to 7-membered ring system which is a member selected from the group consisting of substituted or unsubstituted cycloalkyl, substituted or unsubstituted heterocycloalkyl, substituted or unsubstituted aryl and substituted or unsubstituted heteroaryl;

wherein said fluorophore has the formula:

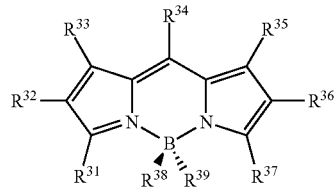

wherein R³¹, R³², R³³, R³⁴, R³⁵, R³⁶ and R³⁷ are members independently selected from the group consisting of H, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein at least one of $R^{31}$, $R^{32}$, $R^{33}$, $R^{34}$, $R^{35}$, $R^{36}$ and $R^{37}$ comprises a bond to the remainder of the compound according to Formula I; and $R^{38}$ and $R^{39}$ are members independently selected from the group consisting of H, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, and $N^{40}R^{41}$ wherein $R^{40}$ and $R^{41}$ are members independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

3. The compound according to claim 1, having a structure according to Formula III:

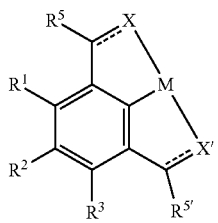

(III)

wherein,

X' is a member selected from the group consisting of X is a moiety selected from $NR^{6'}R^{7'}$, $NR^{6'}$, $PR^{6'}R^{7'}$ and $SR^{6'}$ wherein, $R^{6'}$ and $R^{7'}$ are members independently selected from the group consisting of H, substituted or unsubstituted alkyl, substituted or unsubstituted heteroalkyl, substituted or unsubstituted aryl, and substituted or unsubstituted heteroaryl, and $R^{6'}$ and $R^{7'}$, together with the atoms to which they are bound are optionally joined to form a 5- to 7-membered ring system which is a member selected from the group consisting of substituted or unsubstituted cycloalkyl, substituted or unsubstituted heterocycloalkyl, substituted or unsubstituted aryl and substituted or unsubstituted heteroaryl; and $R^{5'}$ is a member selected from the group consisting of H, substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^{12'}R^{13'}$, $-NR^{12'}R^{13'}$, $-OR^{12'}$, $-S(O)_2R^{12'}$, $-C(O)R^{12'}$, $-COOR^{12'}$, $-CONR^{12'}R^{13'}$, $-S(O)_2OR^{12'}$, $-OC(O)R^{12'}$, $-C(O)NR^{12'}R^{13'}$, $-NR^{12'}C(O)R^{13'}$, $-NR^{12'}SO_2R^{13'}$, $NR^{12'}C(O)NR^{13'}R^{14'}$, $C(NR^{12'})R^{13'}$, and $-NO_2$, wherein, $R^{12'}$, $R^{13'}$ and $R^{14'}$ are members independently selected from the group consisting of H, substituted or unsubstituted alkyl, substituted or unsubstituted heteroalkyl, substituted or unsubstituted aryl, and substituted or unsubstituted heteroaryl, and two or more of $R^{12'}$, $R^{13'}$, and $R^{14'}$, together with the atoms to which they are bound, are optionally joined to form a 5- to 7-membered ring system which is a member selected from the group consisting of substituted or unsubstituted cycloalkyl, substituted or unsubstituted heterocycloalkyl, substituted or unsubstituted aryl and substituted or unsubstituted heteroaryl, and two or more of $R^1$, $R^2$, $R^3$, $R^5$, $R^{12}$, $R^{13}$, $R^{14}$, $R^{12'}$, $R^{13'}$ and $R^{14'}$ are optionally joined to form a 5-7-membered ring system selected from the group consisting of substituted or unsubstituted cycloalkyl, substituted or unsubstituted heterocycloalkyl, substituted or unsubstituted aryl and substituted or unsubstituted heteroaryl.

4. The compound according to claim 1, having a formula which is a member selected from:

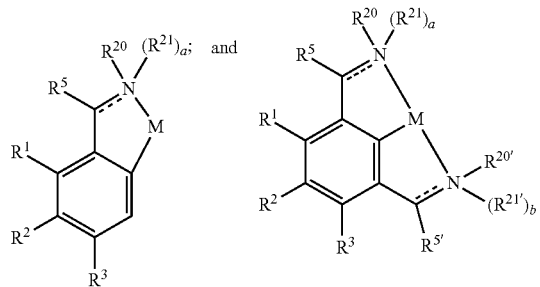

wherein, $R^{20}$, $R^{21}$, $R^{20'}$ and $R^{21'}$ are members independently selected from the group consisting of H, substituted or unsubstituted alkyl, substituted or unsubstituted heteroalkyl, substituted or unsubstituted heterocycloalkyl, substituted or unsubstituted aryl and substituted or unsubstituted heteroaryl; and a and b are selected from the group consisting of the integers 0 and 1, such that when a member selected from the group consisting of a and b is 1, said degree of unsaturation in the relevant ring including $R^{21}$ or $R^{21'}$, respectively, is not present; and $R^{5'}$ is a member selected from the group consisting of H, substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^{12'}R^{13'}$, $-NR^{12'}R^{13'}$, $-OR^{12'}$, $-S(O)_2R^{12'}$, $-C(O)R^{12'}$, $-COOR^{12'}$, $-CONR^{12'}R^{13'}$, $-S(O)_2OR^{12'}$, $-OC(O)R^{12'}$, $-C(O)NR^{12'}R^{13'}$, $-NR^{12'}C(O)R^{13'}$, $-NR^{12'}SO_2R^{13'}$, $NR^{12'}C(O)NR^{13'}R^{14'}$, $C(NR^{12'})R^{13'}$, and $-NO_2$, wherein, $R^{12'}$, $R^{13'}$ and $R^{14'}$ are members independently selected from the group consisting of H, substituted or unsubstituted alkyl, substituted or unsubstituted heteroalkyl, substituted or unsubstituted aryl, and substituted or unsubstituted heteroaryl, and two or more of $R^{12'}$ $R^{13'}$ and $R^{14'}$, together with the atoms to which they are bound, are optionally joined to form a 5- to 7-membered ring system which is a member selected from the group consisting of substituted or unsubstituted cycloalkyl, substituted or unsubstituted heterocycloalkyl, substituted or unsubstituted aryl and substituted or unsubstituted heteroaryl, and two or more of $R^1$, $R^2$, $R^3$, $R^5$, $R^{12}$, $R^{13}$, $R^{14}$, $R^{12'}$, $R^{13'}$ and $R^{14'}$ are optionally joined to form a 5-7-membered ring system selected from the group consisting of substituted or unsubstituted cycloalkyl, substituted or unsubstituted heterocycloalkyl, substituted or unsubstituted aryl and substituted or unsubstituted heteroaryl.

5. The compound according to claim 1, having the formula:

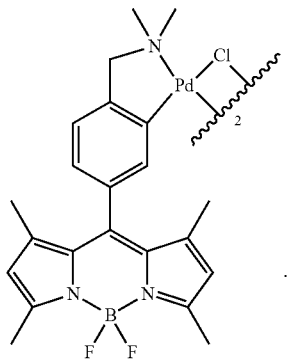

6. The compound according to claim 1, wherein said carbonylation of said compound eliminates said metal, thereby forming a detectably fluorescent compound having the formula:

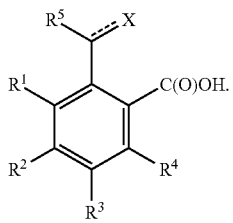

7. A microarray comprising a compound according to claim 1, said compound being conjugated directly to a solid support, conjugated through a linker to a solid support, or conjugated to a carrier species attached to a solid support.

8. The microarray according to claim 7, wherein said compound is conjugated to said carrier species; and said carrier species is a member selected from the group consisting of a biomolecule, a synthetic polymer and combinations thereof.

9. The microarray according to claim 7, wherein said solid support is divided into a first region and a second region, said first region having attached thereto a first said compound and said second region having attached thereto a second said compound.

10. The compound according to claim 1, wherein at least one of $R^{31}$, $R^{32}$, $R^{33}$, $R^{34}$, $R^{35}$, $R^{36}$ and $R^{37}$ is a bond to the remainder of the compound according to Formula I.

* * * * *